United States Patent
Tanaka et al.

(10) Patent No.: US 10,571,412 B2
(45) Date of Patent: Feb. 25, 2020

(54) X-RAY APPARATUS AND STRUCTURE PRODUCTION METHOD

(71) Applicant: NIKON CORPORATION, Tokyo (JP)

(72) Inventors: Toshihisa Tanaka, Yokohama (JP); Shinsuke Takeda, Yokohama (JP); Naoshi Sakaguchi, Kawasaki (JP)

(73) Assignee: Nikon Corporation, Tokyo (JP)

( * ) Notice: Subject to any disclaimer, the term of this patent is extended or adjusted under 35 U.S.C. 154(b) by 231 days.

(21) Appl. No.: 15/502,120

(22) PCT Filed: Aug. 7, 2014

(86) PCT No.: PCT/JP2014/070941
§ 371 (c)(1),
(2) Date: Feb. 6, 2017

(87) PCT Pub. No.: WO2016/021030
PCT Pub. Date: Feb. 11, 2016

(65) Prior Publication Data
US 2017/0219499 A1   Aug. 3, 2017

(51) Int. Cl.
*G01N 23/04* (2018.01)
*G01N 23/046* (2018.01)
*G01N 23/083* (2018.01)

(52) U.S. Cl.
CPC ........... *G01N 23/046* (2013.01); *G01N 23/04* (2013.01); *G01N 23/083* (2013.01);
(Continued)

(58) Field of Classification Search
None
See application file for complete search history.

(56) References Cited

U.S. PATENT DOCUMENTS

| 5,351,278 A | 9/1994 | Koshishiba et al. |
| 5,930,328 A * | 7/1999 | Nakamura ........... A61B 6/4441 378/115 |

(Continued)

FOREIGN PATENT DOCUMENTS

| CN | 1970701 A2 | 9/2008 |
| CN | 101266217 A | 9/2008 |

(Continued)

OTHER PUBLICATIONS

Extended European Search Report and Annex issued by the European Patent Office in Application No. EP 14899421.3, dated Jan. 5, 2018 (8 pages).

(Continued)

*Primary Examiner* — Hoon K Song
(74) *Attorney, Agent, or Firm* — Finnegan, Henderson, Farabow, Garrett & Dunner, L.L.P.

(57) ABSTRACT

An X-ray apparatus includes: a mounting unit upon which an object to be measured is mounted; an X-ray generation unit that irradiates X-rays, from above the mounting unit or from below the mounting unit, to the object to be measured upon the mounting unit; an X-ray detector that acquires a transmission image of the object to be measured being irradiated by the X-rays; a first movement unit that moves at least one of the mounting unit, the X-ray generation unit, and the X-ray detector along a direction of irradiation of the X-rays; a position detection unit that detects a relative position of the mounting unit, the X-ray generation unit, and the X-ray detector; and a calculation unit that calculates a magnification of a transmission image of the object to be measured acquired by the X-ray detector, in a state in which deflection of the mounting unit has occurred while the object to be measured is mounted upon the mounting unit.

24 Claims, 16 Drawing Sheets

(52) U.S. Cl.
CPC ... *G01N 2223/03* (2013.01); *G01N 2223/419* (2013.01); *G01N 2223/505* (2013.01)

(56) References Cited

U.S. PATENT DOCUMENTS

| 7,298,826 | B2 | 11/2007 | Inazuru |
| 2008/0075227 | A1 | 3/2008 | Christoph et al. |
| 2009/0268865 | A1* | 10/2009 | Ren ............... A61B 6/0414 378/37 |
| 2015/0294832 | A1 | 10/2015 | Hakoda et al. |

FOREIGN PATENT DOCUMENTS

| EP | 2 801 815 A1 | 11/2014 |
| EP | 2903398 A1 | 8/2015 |
| JP | 2000-306533 | 11/2000 |
| JP | 2004-45331 | 2/2004 |
| JP | 2005-24508 | 1/2005 |
| JP | 2007-163375 | 6/2007 |
| JP | 2007-309687 A | 11/2007 |
| JP | 2008-241312 | 10/2008 |
| JP | 2009-85667 | 4/2009 |
| JP | 2009-145266 | 7/2009 |
| JP | 2013-140090 A | 7/2013 |
| JP | 2013-174495 | 9/2013 |
| JP | 2014-212011 | 11/2014 |
| TW | 201414360 A | 7/2013 |
| WO | WO 2014/050931 A1 | 8/2016 |

OTHER PUBLICATIONS

International Search Report issued by the Japanese Patent Office in Internatioanl Application No. PCT/JP2014/070941, dated Sep. 2, 2014 (3 pages).
Notification of Reason(s) for Refusal issued by the Japanese Patent Office in corresponding Japanese Application No. 2016-539762, dated Feb. 13, 2018 (4 pages plus 10 page translation).
Notification of Reason(s) for Refusal (Translation) issued by the Japanese Patent Office in corresponding Japanese Application No. 2016-539762, dated Feb. 20, 2018.
Taiwanese Office Action dated Nov. 29, 2018 by the Intellectual Property Office of Taiwan in Taiwanese Application No. 104125190, and the English translation thereof.
Notification of Reasons for Refusal of the counterpart Japanese Patent Application No. 2013-546226 dated Dec. 3, 2019.
Decision of Refusal of the counterpart Taiwanese Patent Application No. 104125190 dated Nov. 26, 2019.

\* cited by examiner

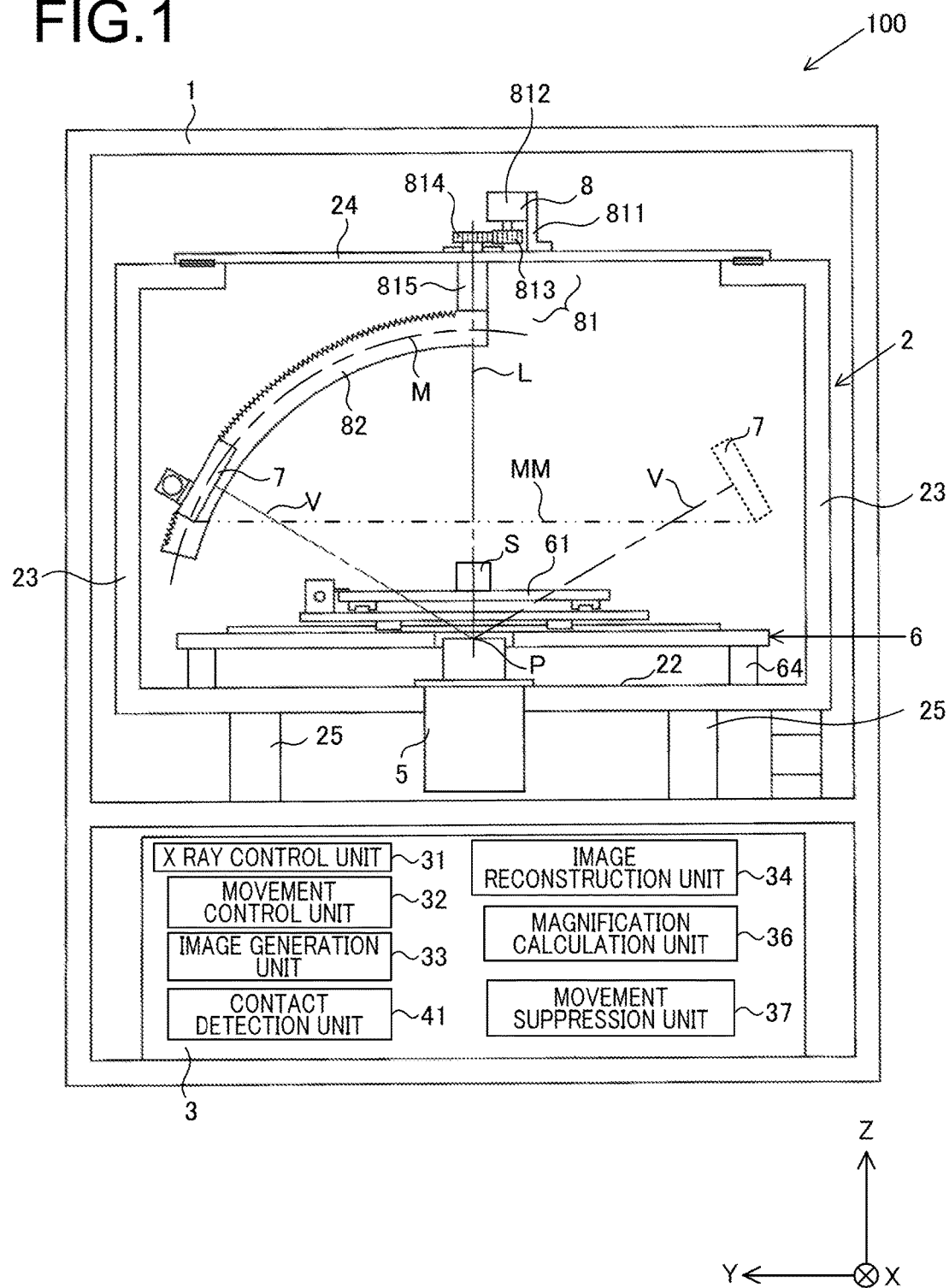

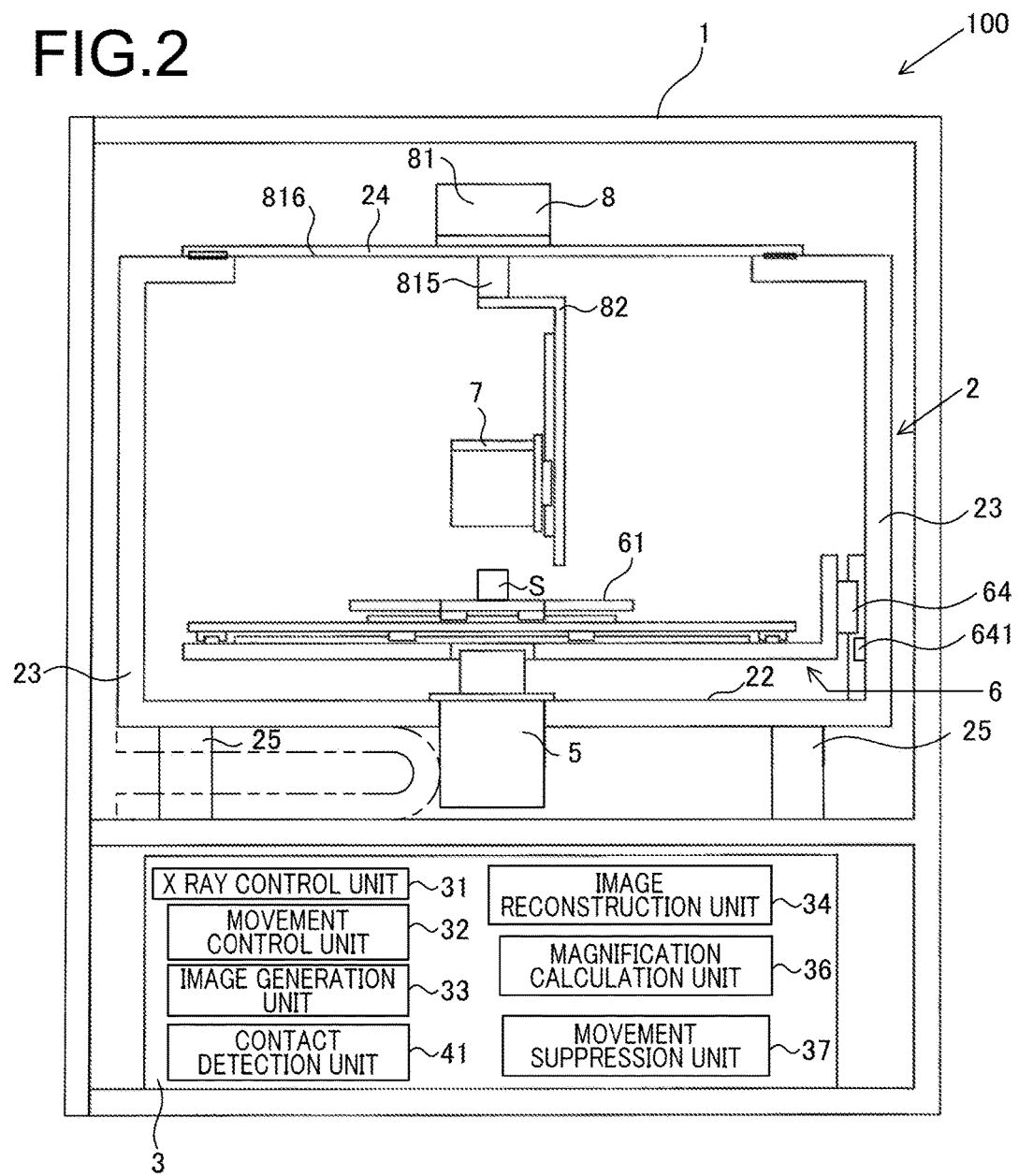
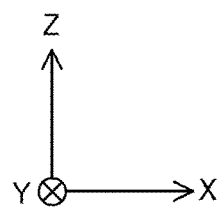

FIG.10
(a) 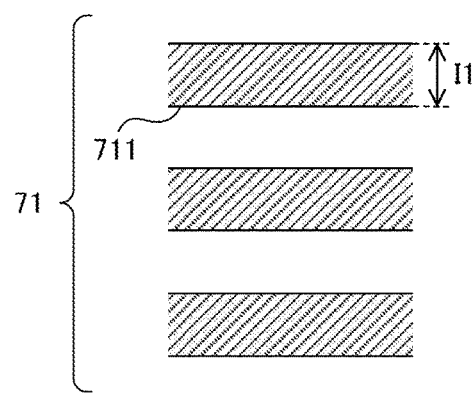
(b) 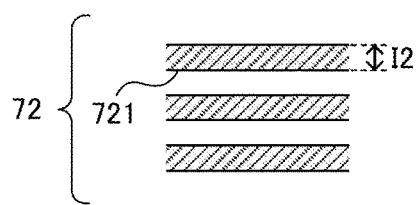

X-RAY APPARATUS AND STRUCTURE PRODUCTION METHOD

This application is a National Stage of International Application number PCT/JP2014/070941, filed Aug. 7, 2014 the content of which is incorporated herein by reference.

TECHNICAL FIELD

The present invention relates to an X-ray apparatus and to a structure production method.

BACKGROUND ART

From the prior art, an X-ray apparatus is per se known (for example, refer to Patent Document #1) in which an X-ray source is disposed so that the optical axis of the X-rays is aligned in the vertical direction, and a mounting table is provided in a horizontal plane.

CITATION LIST

Patent Literature

Patent Document #1: Japanese Patent 4,133,657.

SUMMARY OF INVENTION

Technical Problem

However, there has been the problem that it is not possible to obtain an accurate magnification, since the deflection that occurs in the mounting table when a test specimen to be measured is mounted upon the mounting table varies according to the weight of the test specimen.

Solution to Technical Problem

According to the 1st aspect of the present invention, an X-ray apparatus comprises: a mounting unit upon which an object to be measured is mounted; an X-ray generation unit that irradiates X-rays, from above the mounting unit or from below the mounting unit, towards the object to be measured that is mounted upon the mounting unit; an X-ray detector that acquires a transmission image of the object to be measured that is being irradiated by the X-rays; a first movement unit that moves at least one of the mounting unit, the X-ray generation unit, and the X-ray detector along a direction of irradiation of the X-rays; a position detection unit that detects a relative position of the mounting unit, the X-ray generation unit, and the X-ray detector; and a calculation unit that calculates a magnification of a transmission image of the object to be measured that is acquired by the X-ray detector, in a state in which a deflection of the mounting unit has occurred while the object to be measured is mounted upon the mounting unit.

According to the 2nd aspect of the present invention, it is preferred that in the X-ray apparatus according to the 1st aspect, the first movement unit moves the mounting unit; and the X-ray apparatus further comprises a proximity detection unit that detects contact between or proximity of a deflected region occurred on the mounting unit and the X-ray generation unit; and wherein the calculation unit calculates the magnification of the transmission image of the object to be measured on the basis of the relative position when contact or proximity is detected by the proximity detection unit, in the state in which the object to be measured is mounted upon the mounting unit.

According to the 3rd aspect of the present invention, it is preferred that in the X-ray apparatus according to the 2nd aspect, the X-ray generation unit irradiates the X-rays towards the object to be measured from below the mounting unit; and the proximity detection unit comprises a first electrically conductive member that is provided upon a surface of the mounting unit that opposes the X-ray generation unit and a second electrically conductive member that is provided upon the X-ray generation unit, and detects contact between the first and second conductive members electrically.

According to the 4th aspect of the present invention, it is preferred that in the X-ray apparatus according to any one of the 1st through 3rd aspects, the calculation unit comprises a deflection detection unit that detects the deflection amount of the mounting unit while the object to be measured is mounted upon the mounting unit; and the calculation unit calculates the magnification of the transmission image of the object to be measured on the basis of the relative position detected by the position detection unit and the deflection amount detected by the deflection detection unit.

According to the 5th aspect of the present invention, an X-ray apparatus comprises: a mounting unit upon which an object to be measured is mounted; an X-ray generation unit that irradiates X-rays, from above the mounting unit or from below the mounting unit, towards the object to be measured that is mounted upon the mounting unit; a mark for magnification measurement that is formed upon a mounting surface or upon an underside surface of the mounting unit; an X-ray detector that acquires a transmission image of the object to be measured and a transmission image of the mark for magnification measurement, which are being irradiated by the X-rays; a first movement unit that moves at least one of the mounting unit, the X-ray generation unit, and the X-ray detector along a direction of irradiation of the X-rays; and a calculation unit that calculates a magnification of a transmission image of the object to be measured on the basis of a transmission image of the mark for magnification measurement, among a transmission image of the object to be measured and a transmission image of the mark for magnification measurement detected by the X-ray detector.

According to the 6th aspect of the present invention, it is preferred that in the X-ray apparatus according to the 5th aspect, the mark for magnification measurement is formed upon the mounting surface of the mounting unit.

According to the 7th aspect of the present invention, it is preferred that in the X-ray apparatus according to the 5th aspect, a contact detection unit that detects contact of the mounting unit on the X-ray generation unit, while the first movement unit moves at least one of the mounting unit and the X-ray generation unit; and wherein the X-ray generation unit irradiates the X-rays against the object to be measured from below the mounting unit.

According to the 8th aspect of the present invention, it is preferred that in the X-ray apparatus according to the 7th aspect, the contact detection unit comprises an electrically conductive member that is provided upon the underside surface of the mounting unit, and an electrically conductive member that is provided upon the X-ray generation unit; and the contact detection unit detects contact between the electrically conductive member that is provided upon the underside surface of the mounting unit and the electrically conductive member that is provided upon the X-ray generation unit electrically.

According to the 9th aspect of the present invention, it is preferred that in the X-ray apparatus according to the 7th aspect, the mark for magnification measurement comprises an electrically conductive member that is formed upon the underside surface of the mounting unit.

According to the 10th aspect of the present invention, the X-ray apparatus according to any one of the 5th through 9th aspects may further comprise an extraction unit that extracts a transmission image of the mark for magnification measurement from a transmission image of the object to be measured and a transmission image of the mark for magnification measurement; and wherein the calculation unit calculates the magnification of the transmission image of the object to be measured on the basis of the transmission image of the mark for magnification measurement extracted by the extraction unit.

According to the 11th aspect of the present invention, it is preferred that in the X-ray apparatus according to any one of the 5th through 10th aspects, if distortion has been generated in the mark for magnification measurement with deflection of the mounting unit occurred by mounting of the object to be measured, the calculation unit corrects the magnification of the transmission image of the object to be measured on the basis of the transmission image of the mark for magnification measurement in which the distortion has been generated, and the state of distortion of the mark for magnification measurement.

According to the 12th aspect of the present invention, an X-ray apparatus comprises: a mounting unit upon which an object to be measured is mounted; an X-ray generation unit that irradiates X-rays, from above the mounting unit or from below the mounting unit, towards the object to be measured that is mounted upon the mounting unit; a mark for magnification measurement that is formed upon a mounting surface or upon an underside surface of the mounting unit; an X-ray detector that acquires a transmission image of the object to be measured and a transmission image of the mark for magnification measurement, which are being irradiated by the X-rays; a first movement unit that moves at least one of the mounting unit, the X-ray generation unit, and the X-ray detector along a direction of irradiation of the X-rays; a position detection unit that detects a relative position of the mounting unit, the X-ray generation unit, and the X-ray detector; a first calculation unit that calculates a magnification of a transmission image of the object to be measured on the basis of the relative position detected by the position detection unit; a second calculation unit that calculates the magnification of a transmission image of the object to be measured on the basis of a transmission image of the mark for magnification measurement acquired by the X-ray detector; and a control unit that causes one of the first calculation unit and the second calculation unit to calculate the magnification of the object to be measured.

According to the 13th aspect of the present invention, it is preferred that in the X-ray apparatus according to the 12th aspect, if the magnification corresponding to the relative position detected by the position detection unit is smaller than a predetermined value, the control unit causes the first calculation unit to calculate the magnification of the object to be measured; and, if the magnification corresponding to the relative position detected by the position detection unit is greater than the predetermined value, the control unit causes the second calculation unit to calculate the magnification of the object to be measured.

According to the 14th aspect of the present invention, the X-ray apparatus according to the 12th or the 13th aspect may further comprise a contact detection unit that detects contact of the mounting unit against the X-ray generation unit, while the first movement unit moves at least one of the mounting unit and the X-ray generation unit; and wherein: the X-ray generation unit irradiates the X-rays against the object to be measured from below the mounting unit; the mark for magnification measurement is formed upon the underside surface of the mounting unit; and the contact detection unit detects that the mark for magnification measurement has contacted against the X-ray generation unit.

According to the 15th aspect of the present invention, it is preferred that in the X-ray apparatus according to the 14th aspect, the mark for magnification measurement comprises an electrically conductive member; the X-ray generation unit comprises an electrically conductive member; and the contact detection unit detects contact between the mark for magnification measurement and the electrically conductive member comprised in the X-ray generation unit electrically.

According to the 16th aspect of the present invention, the X-ray apparatus according to any one of the 1st through 15th aspect may further comprise: a second movement unit that moves at least one of the mounting unit and the X-ray generation unit in a plane that intersects a direction of movement by the first movement unit; and a suppression unit that suppresses movement by the second movement unit while the mounting unit and the X-ray generation unit are in mutual contact.

According to the 17th aspect of the present invention, the X-ray apparatus according to any one of the 1st through 16th aspect may further comprise a reconstruction unit that creates internal structural information about the object to be measured on the basis of a plurality of projection data detected by the X-ray detector, in a state in which the positions of the X-ray generation unit and the X-ray detector with respect to the object to be measured are different.

According to the 18th aspect of the present invention, a structure production method comprises: creating design information related to a shape of a structure; forming the structure on the basis of the design information; acquiring shape information by measuring the shape of the structure, which has been formed, by using the X-ray apparatus according to any one of the 1st through 16th aspect; and comparing the shape information that has been acquired and the design information.

According to the 19th aspect of the present invention, the structure production method according to the 18th aspect may further comprise performing re-processing of the structure on the basis of a result of comparison of the shape information and the design information.

According to the 20th aspect of the present invention, it is preferred that in the structure production method according to the 19th aspect, the re-processing of the structure comprises again performing formation of the structure on the basis of the design information.

Advantageous Effects of Invention

According to the present invention, it is possible to calculate the magnification of a transmission image of an object to be measured with good accuracy, even in a state in which deflection has been occurred in the mounting unit due to the object to be measured having been mounted upon the mounting unit.

BRIEF DESCRIPTION OF DRAWINGS

FIG. 1 is an internal elevation view of an X-ray apparatus according to a first embodiment;

FIG. 2 is an internal side view of this X-ray apparatus according to the first embodiment;

FIG. 10 is a figure showing an example of a mark transmission image and a template image that are employed during calculation of the magnification provided by the X-ray apparatus according to this second embodiment;

DESCRIPTION OF EMBODIMENTS

—Embodiment #1—

Embodiments of the present invention will now be explained with reference to the drawings. The X-ray apparatus discussed herein is an X-ray CT (Computerized Tomography) test device that acquires internal information about an object to be measured or the like (for example, its internal structure) in a non-destructive manner by irradiating X-rays upon the object to be measured, and by detecting transmission X-rays that have been transmitted through the object to be measured. If the object to be measured is, for example, an industrial component such as a mechanical component or an electronic component or the like that is to be the subject of measurement, then this X-ray apparatus that components for industrial use is termed an "X-ray CT test device for industrial use".

These embodiments are provided in order to explain the gist of the present invention in concrete terms for better understanding thereof, but, unless particularly so stated, are not intended to be limitative of the present invention in any way.

Figure 3:
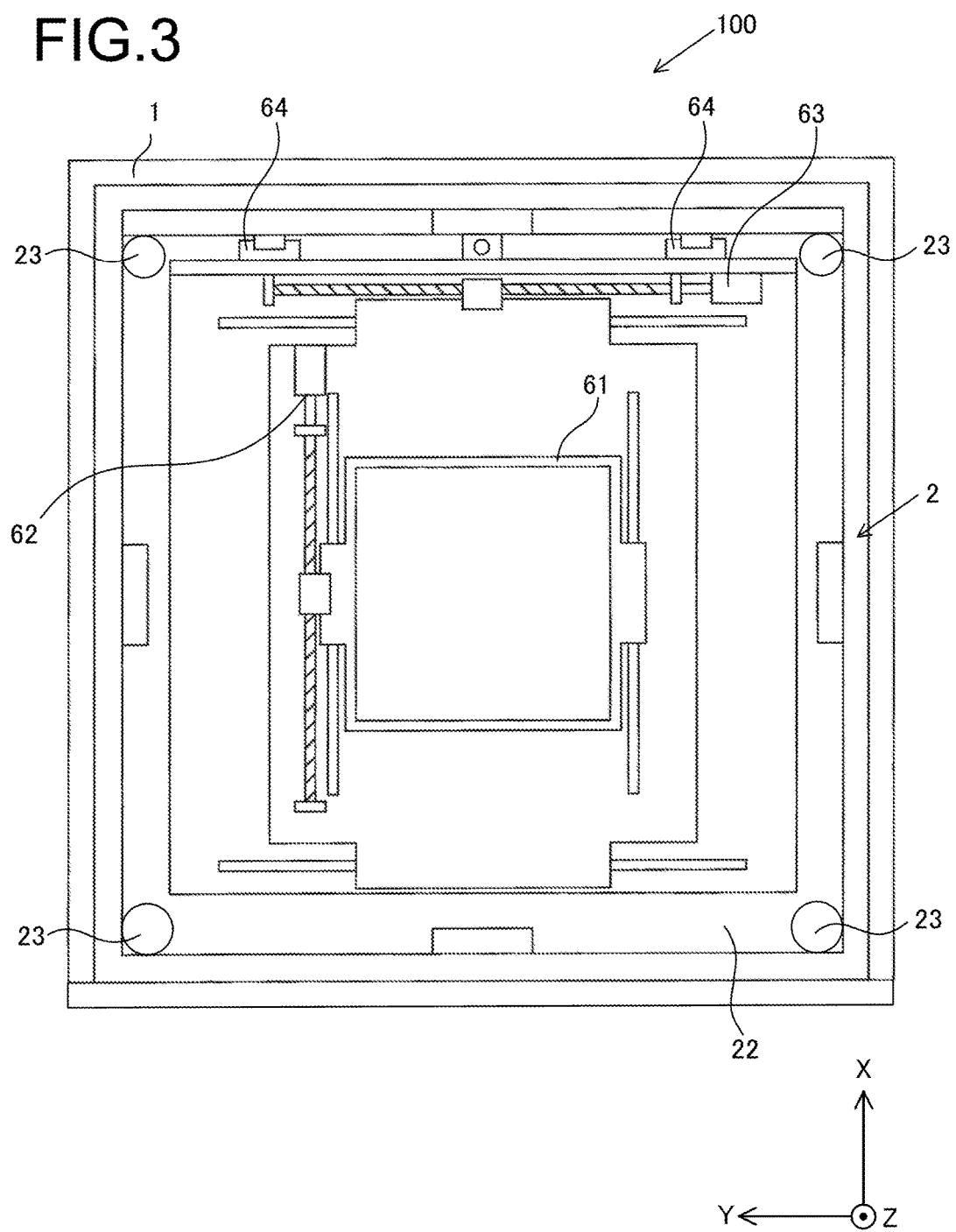
FIG. 3 is an internal plan view of the X-ray apparatus according to the first embodiment.

FIGS. 1 through 3 are figures showing an example of the internal structure of an X-ray apparatus 100 according to this embodiment: FIG. 1 is an internal elevation view of the X-ray apparatus 100; FIG. 2 is an internal side view of the X-ray apparatus 100; and FIG. 3 is an internal plan view of the X-ray apparatus 100. It should be understood that, for the convenience of explanation, a coordinate system is established in the figures, consisting of an X axis, a Y axis, and a Z axis that extends in the vertical direction.

The X-ray apparatus 100 comprises a casing 1, a frame 2, and a control device 3. The casing 1 is disposed upon the floor of a workpiece or the like so that its X-Y plane is substantially horizontal, and the frame 2 and the control device 3 are contained in its interior. In order for X-rays not to leak to its exterior, the casing 1 includes lead as a material.

An X-ray source 5, a mounting unit 6, an X-ray detector 7, and an X-ray detector drive unit 8 are mounted to the frame 2. The frame 2 comprises a bottom base plate 22 that is shaped as rectangular, four struts 23 that are provided at the four corners of the bottom base plate 22 and that extend upward in the Z axis direction, and an attachment member 24 that is provided at the upper ends of the struts 23 for attachment of the X-ray detector drive unit 8. Anti-vibration mounts 25 for attenuating vibrations transmitted to the frame 2 from the exterior of the casing 1 are attached to the lower portion of the bottom base plate 22 (i.e. to its surface in the −Z axis direction). These anti-vibration mounts 25 may, for example, be built from per se known air springs and/or coil springs, singly or in combination. It should be understood that the frame 2 is not limited to being of a type that supports the X-ray detector drive unit 8 on the upper portions of its four struts 23; it may have any structure or shape that may be required for it to be capable of stably supporting the X-ray detector drive unit 8, in other words the X-ray detector 7.

The X-ray source 5 is attached to the bottom base plate 22 of the frame 2, and hangs down from the vicinity of the central portion of the bottom base plate 22. The X-ray source 5 is controlled by the control device 3, and emits X-rays that widen out through a region V-V in a conical shape over a wide angle (i.e. a so-called "conical beam"), with a point P shown in FIG. 1 being the point of emission. This point P of emission and the focal point of the X-ray source 5 coincide. It should be understood that, in the following explanation, the axis parallel to the Z axis and passing through the point P will be termed the "reference axis L". In this embodiment, the X-ray source 5 is provided so that the reference axis L passes through the center of the frame 2. Moreover, it should be understood that the X-ray source 5 may be built as a transmission type X-ray source, or it may be built as a reflection type X-ray source.

A tip of the body of the X-ray source 5 at side of the +Z axis direction is made from an electrically conductive metallic material (such as, for example, brass, tungsten alloy, copper, or the like). If the X-ray source 5 is built as a transparent type X-ray source, then the tip at the side of the +Z axis direction may be a target made from, for example, a material that includes tungsten, in order for X-rays to be generated by the arrival of electrons from a filament. Furthermore, if the X-ray source 5 has a protective member that is an electrically conductive member made from beryllium or the like in order to protect the target from the outside, then this protective member becomes the tip at the side of the +Z axis direction of the X-ray source 5. The X-ray source 5 may, for example, emit X-rays of at least one of the following types: ultra soft X-rays of about 50 eV, soft X-rays of about 0.1 to 2 keV, X-rays of about 2 to 20 keV, and hard X-rays of about 20 to 100 keV.

The mounting unit 6 comprises a mounting table 61 for mounting the object S to be measured, and an X axis movement mechanism 62, a Y axis movement mechanism 63, and a Z axis movement mechanism 64 for respectively moving the mounting table 61 in the X axis direction, in the Y axis direction, and in the Z axis direction (refer to FIG. 3). The X axis movement mechanism 62 and the Y axis movement mechanism 63 are both built from a motor, rails, a slider, and so on, and, according to control by the control device 3, respectively move the mounting table 61 along the X axis direction and along the Y axis direction. And the Z axis movement mechanism 64 is built from a motor, rails, a slider, and so on, and, according to control by the control device 3, moves the mounting table 61 along the Z axis direction. A Z position detector 641 (refer to FIG. 2) is an encoder that detects the position of the mounting table 61 to which it has been moved by the Z axis movement mechanism 64 in the Z axis direction, and that outputs a signal specifying the position that it has detected to the control device 3 (hereinafter, this will be termed the "Z position signal"). It should be understood that the details of the mounting table 6 will be described hereinafter.

The X-ray detector 7 comprises a scintillator section that includes a per se known scintillation substance, a photomultiplier tube, and a light reception section and so on, and receives X-rays including transmission X-rays that have been emitted from the X-ray source 5 and that have passed through the object S to be measured, which is mounted upon the mounting table 61. After having converted the energy in the received X-rays to optical energy, this X-ray detector 7 converts that optical energy to electrical energy, which it outputs as an electrical signal. It should be understood that it would also be acceptable to arrange for the X-ray detector 7 to convert the energy of the incident X-rays directly to an electrical signal, without performing any intermediate conversion to optical energy. Furthermore, the X-ray detector 7 has a plurality of pixels, and those pixels are arranged in a two-dimensional array. Due to this, it is possible to acquire the intensity distribution of the X-rays that have been emitted from the X-ray source 5 and that have passed through the object S to be measured all at once. Accordingly, it is possible to acquire an entire projection image of the object S to be measured with one imaging.

The X-ray detector drive unit 8 moves the X-ray detector 7 upon a rotational path centered upon the reference axis L. This X-ray detector drive unit 8 comprises a rotation mechanism 81 that is attached to the attachment member 24 of the frame 2, and a circular arcuate stage 82 that is rotated by this rotation mechanism 81. The rotation mechanism 81 comprises an attachment plate 811, a motor 812 that is attached to the attachment plate 811, a first gear 813 that is rotated by the motor 812, a second gear 814 that is meshed with the first gear 813, and a hollow rotation shaft 815. Due to the rotation shaft 815 being rotated by the second gear 814 around the reference axis L as a center, the circular arcuate stage 82 that is fixed to the lower portion of the rotation shaft 815 is rotated, and the X-ray detector 7, which is movably provided upon the circular arcuate stage 82, is rotated along a rotation path MM around the reference axis L as a center.

The circular arcuate stage 82 is a plate that is formed so as to have a predetermined length along a circular arc, with the point P that is the emission point of the X-rays being the center. A guide rail and/or a slider or the like are provided upon the circular arcuate stage 82, and the X-ray detector 7 described above is attached so as to be movable by a motor or the like along a circular arcuate path M of the circular arcuate stage 82. Due to this, by rotating the circular arcuate stage 82 with the rotation mechanism 81, it becomes possible to perform adjustment so as to move the stage 82 in a circular motion, so that the path of the X-ray detector 7 tracks at the same desired height around the side surface of a cone whose vertex is the point P (and upon the same surface of that cone, toward the +Z axis direction).

Since, by providing the structure described above, it is possible to move the X-ray detector 7, along the rotation path MM whose center is the reference axis L and along the circular arcuate path M whose center is the X-ray emission point P, to any desired location upon a spherical surface that is centered upon the point of emission P of the X-rays, accordingly it is possible for the user to perform detecting image of the object S to be measured from any desired detecting position and at any desired detecting angle. Moreover, it is possible to perform detecting image of the object S to be measured at any desired magnification by moving the mounting table 61 in the Z axis direction.

The control device 3 includes a microprocessor and peripheral circuitry thereof and so on, and controls the various sections of the X-ray apparatus 100 by loading and executing a control program that is stored in advance in a storage medium not shown in the figures (for example, a flash memory or the like). The control device 3 comprises an X-ray control unit 31, a movement control unit 32, an image generation unit 33, an image reconstruction unit 34, a magnification calculation unit 36, a movement suppression unit 37, and a contact detection unit 41. The X-ray control unit 31 controls the output of the X-ray source 5, and the movement control unit 32 controls the movement operation of the mounting unit 6. The image generation unit 33 generates projected X-ray image data for the object S to be measured on the basis of electrical signals that are outputted from the X-ray detector 7, and the image reconstruction unit 34 performs per se known image reconstruction processing on the basis of the projection image data for the object S to be measured from different directions of projection, thereby creating a reconstructed image. Three dimensional data that specifies the internal structure (i.e. the cross sectional structure) of the object S to be measured is created by this reconstructed image. In this case, a back projection method, a filtered back projection method, an iterative reconstruction method, and so on are possible methods for creating the reconstructed image.

On the basis of the Z position signal outputted from the Z position detector 641, in other words on the basis of the position of the mounting table 61 in the Z axis direction, the magnification calculation unit 36 calculates the magnification of the projection image data or of the reconstructed image of the object S to be measured which is mounted upon the mounting table 61. And, if a mounting plate for the object to be measured of the mounting table 61, which will be described hereinafter, contacts to the X-ray source 5, then the movement suppression unit 37 prevents driving of the X axis movement mechanism 62 and of the Y axis movement mechanism 63, and thus ensures that movement of the mounting table 61 in the X-Y plane cannot be performed. The contact detection unit 41 detects the fact that the X-ray source 5 and the mounting plate for the object to be measured of the mounting table 61 have come into contact. It should be understood that the details of the processing performed by the magnification calculation unit 36 will be described and explained hereinafter.

Figure 4:
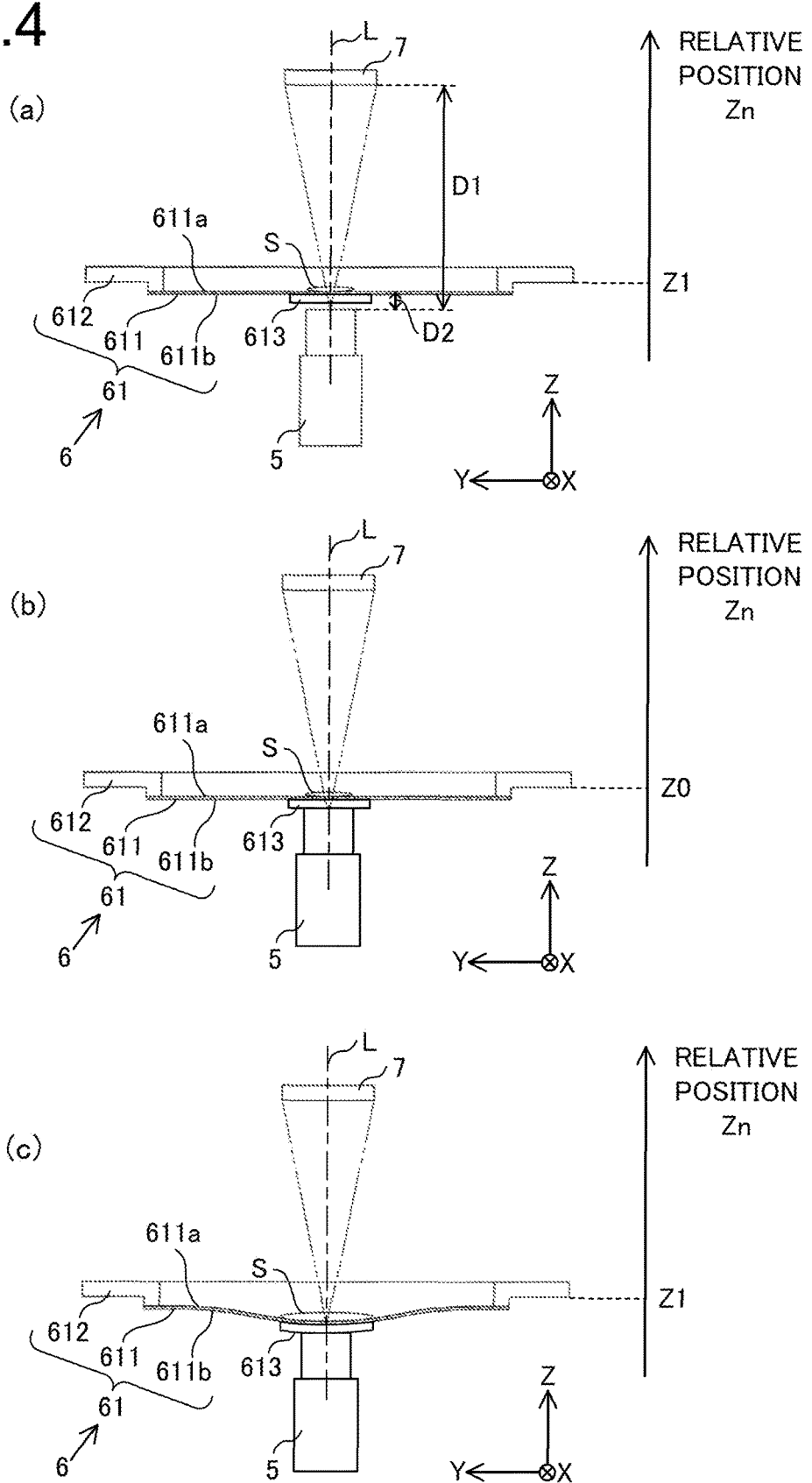
FIG. 4 is a figure for explanation of deflections occurred in a mounting table and in a measured object mounting plate that are provided to this X-ray apparatus according to the first embodiment.

The details of the mounting unit 6 will now be explained with reference to FIG. 4. FIG. 4 consists of side views showing the positional relationships in the Z axis direction between the X-ray source 5, the mounting unit 6, and the X-ray detector 7. It should be understood that, in FIG. 4, among the members that make up the mounting unit 6, members that are related to the mounting table 61 are shown as representative, and, in order to simplify the explanation, a case is shown in which the X-ray detector 7 is positioned upon the reference axis L. Moreover in FIG. 4, as shown in the figure, a coordinate system is established that is similar to that of FIGS. 1 through 3, and that consists of an X axis, a Y axis, and a Z axis.

As shown in FIG. 4, the mounting table 61 comprises a mounting plate 611 for supporting the object to be measured, a mounting plate support unit 612, and a contact sensitive unit 613. The mounting plate 611 for the object to be measured may, for example, be made from CFRP (carbon fiber reinforced plastic) or the like, and the object S to be measured is mounted upon the upper side of this measured object mounting plate 611 (i.e. upon its side that faces in the +Z axis direction). The measured object mounting plate 611 is formed to be thin along the Z axis direction, in order for the magnification of the projection image that is projected upon the X-ray detector 7 to be as great as possible, and in order for the absorption by the plate of the X-rays emitted from the X-ray source 5 to be as low as possible.

The mounting plate support unit 612 is formed in the shape of a frame, and supports the measured object mounting plate 611 around its external peripheral portion. And the mounting plate support unit 612 is moved by the X axis movement mechanism 62, by the Y axis movement mechanism 63, and by the Z axis movement mechanism 64 along the X axis direction, the Y axis direction, and the Z axis direction respectively, and, due to this movement of the mounting plate support unit 612, the measured object mounting plate 611 that is supported by the mounting plate support unit 612 and the object S to be measured that is mounted upon the measured object mounting plate 611 are moved together therewith along the X axis direction, along the Y axis direction, and along the Z axis direction. It should be understood that while, in FIG. 4, an example is shown in which the mounting plate support unit 612 supports the measured object mounting plate 611 from its +Z axis side, the method for support by the mounting plate support unit 612 is not limited to that of the example shown in FIG. 4. For example, a construction in which the mounting plate support unit 612 is attached to the measured object mounting plate 611 from its −Z axis side, or a construction in which the measured object mounting plate 611 is supported by being sandwiched from its +Z axis side and from its −Z axis side, are also to be considered as modes that are included within the scope of the present invention.

The contact sensitive unit 613 is built from a conductor in the form of a thin layer or the like, and is provided on the −Z axis side of the measured object mounting plate 611, in other words on its side that opposes the X-ray source 5. When, due to motion of the mounting plate support unit 612 in the Z axis direction, the surface of the measured object mounting plate 611 in the −Z axis direction and the X-ray source 5 come into mutual contact, the contact sensitive unit 613 becomes electrically continuous with the tip of the X-ray source 5 in the +Z axis direction, which as described above is made as a conductor. The contact detection unit 41 mentioned above of the control device 3 detects the value of the resistance between the contact sensitive unit 613 and the tip of the X-ray source in the +Z axis direction, and determines that the measured object mounting plate 611 and the X-ray source 5 are in mutual contact if this resistance value is substantially zero [Ω], while determining that the measured object mounting plate 611 and the X-ray source 5 are not in mutual contact if this resistance value is substantially infinite [Ω].

In the subsequent explanation, the surface of the measured object mounting plate 611 towards the +Z axis side, in other words the surface thereof on the side on which the object S to be measured is mounted, will be termed the mounting surface 611a, and its surface towards the −Z axis side, in other words its surface on the side where the contact sensitive unit 613 is provided, will be termed the underside surface 611b. Moreover, it will be acceptable for the contact sensitive unit 613 to be provided over the entire underside surface 611b; or, alternatively, it would also be acceptable for the contact sensitive unit 613 to be provided only at a region of the underside surface 611b where, due to movement of the measured object mounting plate 611 in the Z axis direction, the possibility of coming into contact with the X-ray source 5 is high (for example, in the vicinity of the central portion of the rear surface 611b).

Since, as described above, the measured object mounting plate 611 is thin, accordingly, when the object S to be measured has been mounted upon its mounting surface 611a, some deflection in the −Z axis direction is generated in the measured object mounting plate 611 due to the weight of the object S to be measured. When deflection takes place in the measured object mounting plate 611, error occurs between the magnification that is calculated by the magnification calculation unit 36 on the basis of the position of the mounting table 61 in the Z axis direction outputted from the Z position detection unit 641, and the actual magnification. However, the X-ray apparatus 100 of this embodiment is provided with the capability of correcting such magnification errors that originate in deflection of the measured object mounting plate 611 occurred due to the object S to be measured being mounted thereupon.

Now, this correction of magnification error will be explained.

—The Relationship Between the Deflection and the Magnification Error—

FIGS. 4(a) and 4(b) show a state in which no deflection has been occurred in the measured object mounting plate 611, while FIG. 4(c) shows a state in which some deflection has been occurred in the measured object mounting plate 611. Thus, it should be understood that FIGS. 4(a) and 4(b) are figures that schematically show states in which it is hypothesized that no deflection of the measured object mounting plate 611 is taking place even though the object S to be measured is mounted thereupon, and that FIG. 4(b) is a figure showing a state in which the measured object mounting plate 611 is in contact with the X-ray source 5. The magnification of the transmission image of the object S to be measured included in the projection image or in the reconstructed image is determined by the distance D1 between the emission point P of the X-ray source 5 and the detecting surface of the X-ray detector 7, and the distance D2 between the emission point P and the object S to be measured. The magnification of the transmission image of the object S to be measured increases according to decrease of the distance D2 between the emission point P of the X-ray source 5 and the object S to be measured, and increases according to increase of the distance D1 between the emission point P and the detecting surface of the X-ray detector 7. In other words, the magnification is given by D1/D2. In FIG. 4(b), since the measured object mounting plate 611 and the X-ray source 5 are in mutual contact, accordingly the distance D2 from end surface of the object S to be measured at a side of the −Z axis corresponds to the thickness of the measured object mounting plate 611. That is to say, the distance D2 becomes minimum, and at this time the magnification of the transmission image of the object S to be measured becomes maximum. It should be understood that this maximum magnification is a value that is determined by the construction of the X-ray apparatus 100.

As described above, this X-ray apparatus 100 has a structure in which the mounting table 61 moves along the Z axis direction. In other words, the mounting plate support unit 612 that supports the measured object mounting plate 611 is moved by the Z axis movement mechanism 64. The Z position detection unit 641 detects the relative position of the mounting plate support unit 612, which is moved by the Z axis movement mechanism 64, with respect to the X-ray source 5. As shown in FIG. 4(b), when the measured object mounting plate 611 is in contact with the X-ray source 5 in the state in which no deflection is being occurred in the measured object mounting plate 611, its relative position with respect to the X-ray source 5 becomes z0, as detected by the Z position detection unit 641. Moreover, in the state in which no deflection is being occurred in the measured object mounting plate 611, in any position of the mounting table 61 in which the measured object mounting plate 611 does not contact against the X-ray source 5, the relative position as detected by the Z position detection unit 641 will be taken as being z1 (refer to FIG. 4(a)).

The magnification calculation unit 36 calculates the magnification of the transmission image of the object S to be measured on the basis of the relative positions z0 and z1 of the measured object mounting plate 611 detected by the Z position detection unit 641. In this case, a correspondence is established between the relative positions z0 and z1 and the magnification of the transmission image of the object S to be measured, and this correspondence is stored in advance as a data table in a predetermined storage region (not shown in the figures); and the magnification calculation unit 36 determines the magnification by referring to the data table described above on the basis of the relative positions z0 and z1 that correspond to the Z position signal outputted from the Z position detection unit 641. It should be understood that, as described above, the magnification of the transmission image of the object S to be measured becomes maximum when the relative position z0 corresponds to the state in which the measured object mounting plate 611 and the X-ray source 5 are in contact.

However actually, as shown in FIG. 4(c), a deflection in the −Z axis direction is occurred in the measured object mounting plate 611 due to the object S to be measured being mounted thereupon. FIG. 4(c) shows the state in which the measured object mounting plate 611, in which deflection has been occurred, is in contact with the X-ray source 5. At this time, its relative position with respect to the X-ray source 5 as detected by the Z position detection unit 641 becomes z1. In other words, in the state of FIG. 4(a), a case is shown in which the object to be measured S has been replaced by a heavier object, so that the measured object mounting plate 611 just contacts to the X-ray source 5. Since, in this case, the measured object mounting plate 611 and the X-ray source 5 are in mutual contact, accordingly the actual magnification of the transmission image of the object S to be measured becomes maximum. However, since the relative position detected by the Z position detection unit 641 is z1, accordingly the magnification of the transmission image of the object S to be measured that, as described above, is calculated by the magnification calculation unit 36 by reference to the data table does not become maximum. In other words, an error occurs between the magnification of the transmission image of the object S to be measured that is calculated by the magnification calculation unit 36, and the actual magnification of the transmission image of the object S to be measured.

Figure 5:
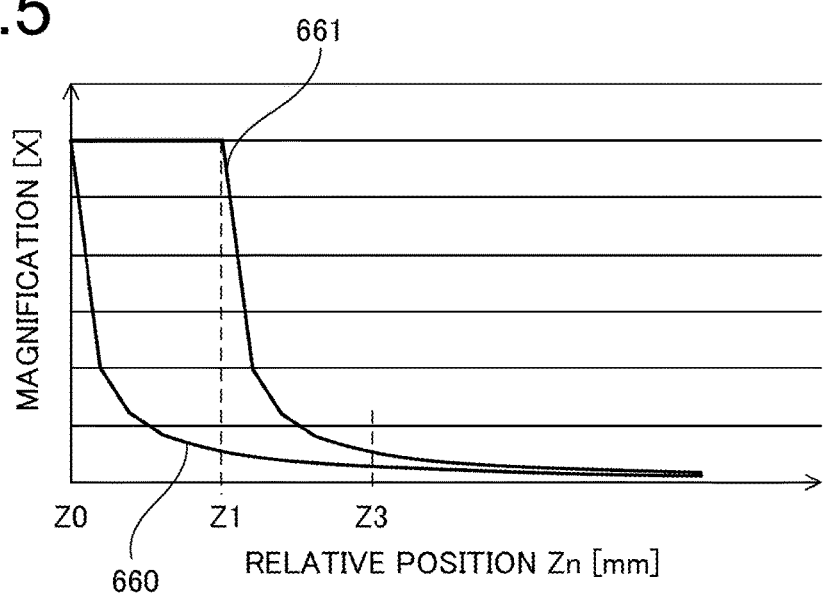
FIG. 5 is a figure showing a relationship between the magnification of a transmission image and a relative position when no deflection is being occurred in the measured object mounting plate, and a similar relationship between the magnification of the transmission image and the relative position when such deflection is being occurred.

The relationship between the magnification of the transmission image of the object S to be measured and the relative value with respect to the X-ray source 5 when no deflection is being occurred in the measured object mounting plate 611, and the relationship between the magnification of the transmission image of the object S to be measured and the relative position with respect to the X-ray source 5 when such a deflection is being occurred, are shown in FIG. 5. In FIG. 5, the relationship when no deflection is being occurred in the measured object mounting plate 611 is denoted by 660, while the relationship when such a deflection is being occurred is denoted by 661. As shown in FIG. 5, in the relationship 661, while the relative position with respect to the X-ray source 5 is between z0 and z1, the magnification remains constant at the maximum magnification, while, when the relative position with respect to the X-ray source 5 is greater than z1, the magnification decreases along with increase of the relative position. On the other hand, in the relationship 660, the magnification decreases according to increase from z0 of the relative position with respect to the X-ray source 5.

As shown in FIG. 5, when deflection is occurred in the measured object mounting plate 611, error occurs in the magnification of the transmission image of the object S to be measured over the entire scope of the relative position with respect to the X-ray source 5 as detected by the Z position detection unit 641. In particular, the influence of this error originating in deflection is large when the X-ray source and the measured object mounting plate 611 are proximate one another in the Z axis direction. Furthermore, when the relative position with respect to the X-ray source 5 detected by the Z position detection unit 641 is between z0 and z1, since the measured object mounting plate 611 is in a state of being in contact with the X-ray source 5, accordingly, even if the mounting plate support unit 612 is moved by the Z axis movement mechanism 64, the magnification of the transmission image of the object S to be measured remains at the maximum magnification, and does not change.

—The Magnification Error Correction Processing—

Error in the magnification of the transmission image of the object S to be measured due to influence of deflection of the measured object mounting plate 611 is corrected by the correction processing that will now be explained. The magnification calculation unit 36 corrects the magnification that has been determined using the data table described above by employing the relative position z1 with respect to the X-ray source 5 detected by the Z position detection unit 641 at the time point that a signal for detection of contact between the measured object mounting plate 611 and the X-ray source 5 is inputted by the contact detection unit 41. In other words, a correspondence between the relative position z1 with respect to the X-ray source 5 detected by the Z position detector 641 when the measured object mounting plate 611 and the X-ray source 5 come into contact, and the maximum magnification of the transmission image of the object S to be measured, is stored in a memory (not shown in the figures). This processing is performed as measurement pre-processing, before measurement of the internal structure of the object S to be measured is begun. Moreover, this processing is also performed if contact between the measured object mounting plate 611 and the X-ray source 5 due to movement of the mounting plate support unit 612 in order to change the magnification of the transmission image of the object S to be measured during measurement of the internal structure of the object S to be measured has been detected.

When as described above the relative position z1 when the measured object mounting plate 611 and the X-ray source 5 are in contact has been stored in the memory, the control device 3 drives the Z axis movement mechanism 64 so as to move the mounting plate support unit 612 to a predetermined target position in the Z axis direction, in order to measure the internal structure of the object S to be measured.

The magnification calculation unit 36 subtracts the relative position z1 when the measured object mounting plate 611 and the X-ray source 5 are in mutual contact from the relative position zn that is detected by the Z position detection unit 641 at the target position. And, on the basis of this value obtained by subtracting the relative position z1 from the relative position zn, the magnification calculation unit 36 reads out the corresponding magnification from the data table, and thereby determines the magnification of the transmission image of the object S to be measured. By doing this, the magnification of the transmission image of the object S to be measured is obtained in an accurate manner in a state in which a deflection corresponding to the weight of the object S to be measured is occurred in the measured object mounting plate 611. Furthermore if, even during the measurement of the object S to be measured, it is detected that the measured object mounting plate 611 and the X-ray source 5 have come into contact, then the magnification calculation unit 36 performs correction processing for the magnification error described above. Due to this, the magnification of the transmission image of the object S to be measured is obtained in an accurate manner, even if there is some fluctuation of the amount of deflection occurred in the measured object mounting plate 611 due to various conditions during measurement (for example the temperature environment or the like).

In this embodiment, measurement of the object S to be measured is performed when, by doing as described above, the object S to be measured is moved to a target position in which the magnification that is desired by the user of the transmission image of the object S to be measured is obtained. The X-ray control unit 51 of the control device 3 controls the output of the X-ray source 5 and irradiates X-rays upon the object S to be measured, while the movement control unit 32 of the control device 3 moves the X-ray detector 7 via the X-ray detector drive unit 8 to any desired location upon the spherical surface centered upon the X-ray emission point P. And, for each one of predetermined positions upon the spherical surface centered upon the X-ray emission point P, the X-ray detector 7 detects the transmitted X-rays emitted from the X-ray source 5 that have passed through the object S to be measured, and outputs a corresponding electrical signal to the control device 3.

Each of the X axis movement mechanism 62, the Y axis movement mechanism 63, the rotation mechanism 81, and the X-ray detector drive unit 8 that shifts the X-ray detector 7 upon the circular arcuate stage 82 comprises encoders (not shown in the figures). The control device 3 is able to acquire information specifying the position of the mounting unit 6 and the X-ray detector 7 on the basis of the outputs from the encoders described above, and on the basis of the output from the Z position detection unit 641. And, while acquiring this position information, the generation unit 33 is able to generate projection image data, which is an X-ray transmission image detected by the X-ray detector 7, and is able to reconstruct the cross sectional structure of the object S to be measured on the basis of this projection image data. In this case, the rotation of the rotation shaft 815 by the X-ray detector drive unit 8 and the generation of projection image data from the X-ray detector 7 by the image generation unit 33 are controlled together by the control device 3, and the image reconstruction unit 34 acquires projection image data of the object S to be measured from a plurality of different directions captured by the X-ray detector 7 via the image generation unit 33. Moreover, the image reconstruction unit 34 acquires the outputs from the encoders and the output from the Z position detection unit 641 via the movement control unit 32, and, on the basis of these outputs and the projection image data, generates three dimensional data, which is the internal structure (i.e. the cross sectional structure) of the object S to be measured, according to a per se known Feldkamp back projection method. It should be understood that, for the image reconstruction processing, it would also be acceptable to use an iterative reconstruction method or the like. This three dimensional data representing the internal structure of the object S to be measured that has thus been generated is displayed upon a display monitor (not shown in the figures).

It should be understood that, during the measurement pre-processing and the measurement processing described above, if it is determined by the contact detection unit 41 that the measured object mounting plate 611 and the X-ray source 5 are in mutual contact, then the movement suppression unit 37 stops (i.e. prevents) driving of the X axis movement mechanism 62 and the Y axis movement mechanism 63. And, when it is decided by the contact detection unit 41 that they are not in contact, then the movement suppression unit 41 cancels the suppression of driving of the X axis movement mechanism 62 and the Y axis movement mechanism 63, so that the X axis movement mechanism 62 and the Y axis movement mechanism 63 come to be driven according to the control signals from the movement control unit 32. In other words, since movement in the X-Y plane is suppressed in the state in which the measured object mounting plate 611 and the X-ray source 5 are in mutual contact, accordingly, along with preventing damage to the object mounting plate 611, also the occurrence of positional deviation of the object S to be measured which is mounted upon the measured object mounting plate 611 due to vibration or the like is prevented. This action is not to be considered as being limited to suppression by the movement suppression unit 37 of the driving of the X axis movement mechanism 62 and the Y axis movement mechanism 63. For example, the provision of a structure in which, when mutual contact between the measured object mounting plate 611 and the X-ray source 5 has been detected, by issuing a warning to the user by employing a warning sound or a message or the like, he is urged not to move the measured object mounting plate 611 in the state in which it is in contact with the X-ray source 5, is also to be understood as being included as an aspect of the present invention.

Figure 6:
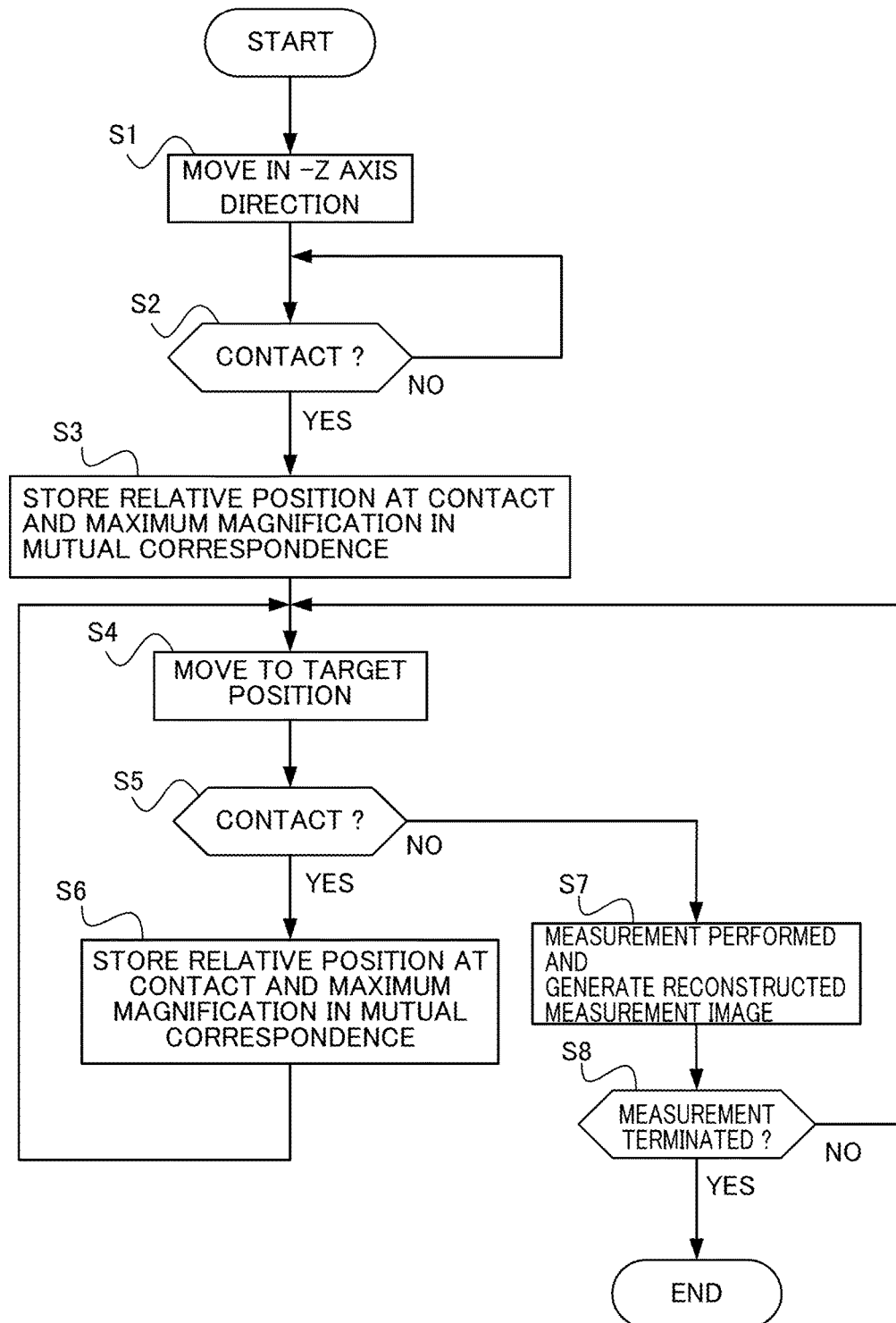
FIG. 6 is a flow chart for explanation of the operation of this X-ray apparatus according to the first embodiment.

The operation performed by this X-ray apparatus 100 will now be explained with reference to the flow chart of FIG. 6. The processing shown in the flow chart of FIG. 6 is performed by the control device 3 executing a program. This program is stored in a memory (not shown in the figures), and is started by the control device 3 and executed when the object S to be measured is mounted upon the measured object mounting plate 611, and actuation to start operation is performed by the user.

In step S1, the Z axis movement mechanism 64 is driven and the mounting plate support unit 612 is moved in the −Z axis direction in the state in which the object S to be measured is mounted upon the measured object mounting plate 611, and then the flow of control proceeds to step S2. In step S2, a decision is made as to whether or not the measured object mounting plate 611 is in contact with the X-ray source 5. If the measured object mounting plate 611 is in contact with the X-ray source 5, in other words if such contact is detected by the contact detection unit 41, then an affirmative decision is reached in step S2 and the flow of control proceeds to step S3. It should be understood that, in this case, the movement suppression unit 37 stops the driving of the X axis movement mechanism 62 and of the Y axis movement mechanism 63. But if the measured object mounting plate 611 is not in contact with the X-ray source 5, in other words if such contact is not detected by the contact detection unit 41, then a negative decision is reached in step S2, and the mounting plate support unit 612 is moved in the −Z axis direction until contact between the measured object mounting plate 611 and the X-ray source 5 is detected.

In step S3 when contact has been detected by the contact detection unit 41, the relative position z1 with respect to the X-ray source 5 detected by the Z position detection unit 641 is stored in the memory in correspondence with the maximum magnification of the transmission image of the object S to be measured, and then the flow of control proceeds to step S4. It should be understood that the processing in steps S1 through S3 corresponds to the measurement pre-processing described above. Then in step S4, in order to measure the internal structure of the object S to be measured, the Z axis movement mechanism 64 is driven, and, in the state in which the object S to be measured is mounted upon the measured object mounting plate 611, the mounting plate support unit 612 is moved to the target position, and then the flow of control proceeds to step S5.

In step S5, in a similar manner to step S2, a decision is made as to whether or not the measured object mounting plate 611 is in contact with the X-ray source 5. In other words, a decision is made as to whether or not a fluctuation in the amount of deflection of the measured object mounting plate 611 is taking place during measurement, due to change of the temperature environment or the like, or due to change over time or the like.

If the measured object mounting plate 611 is in contact with the X-ray source 5, in other words if contact has been detected by the contact detection unit 41, then an affirmative decision is reached in step S5 and the flow of control proceeds to step S6. In this case, the movement suppression unit 37 stops the driving of the X axis movement mechanism 62 and of the Y axis movement mechanism 63. But if the measured object mounting plate 611 is not in contact with the X-ray source 5, in other words if contact is not being detected by the contact detection unit 41, then a negative decision is reached in step S5 and the flow of control is transferred to step S7. In step S6, in a similar manner to the case in step S3, the relative position z1 detected by the Z position detection unit 641 when contact is detected by the contact detection unit 41 is stored in the memory in correspondence with the maximum magnification of the transmission image, and then the flow of control returns to step S4.

In step S7, measurement of the internal structure of the object S to be measured is performed, in other words a reconstructed image is generated on the basis of the electrical signals outputted from the X-ray detector 7, and then the flow of control proceeds to step S8. In step S8, a decision is made as to whether or not measurement has been terminated. If actuation to terminate the measurement of the internal structure of the object S to be measured has been performed by the user, then an affirmative decision is reached in step S8 and this processing flow ends. But if actuation to terminate the measurement of the internal structure of the object S to be measured has not been performed by the user, then a negative decision is reached in step S8 and the flow of control returns to step S4.

According to the X-ray apparatus according to the first embodiment of the present invention described above, the following beneficial operational effects may be obtained.

(1) The Z position detection unit 641 detects the relative position of the mounting plate support unit 612 that supports the measured object mounting plate 611 of the mounting table 61 and the X-ray source 5. And the magnification calculation unit 36 calculates the magnification of the transmission image of the object S to be measured that is acquired by the X-ray detector 7, in the state in which deflection of the measured object mounting plate 611, originating when the object S to be measured was mounted upon the measured object mounting plate 611, is taking place. The contact detection unit 41 detects contact between the measured object mounting plate 611 and the X-ray source 5 originating in such deflection. And when, in the state in which the object S to be measured has been mounted upon the measured object mounting plate 611, contact is detected by the contact detection unit 41, then the magnification calculation unit 36 corrects the magnification of the transmission image of the object S to be measured on the basis of the relative position with respect to the X-ray source 5 detected by the Z position detection unit 641. Accordingly, even if a different deflection amount of the measured object mounting plate 611 is occurred corresponding to the weight of the object S to be measured, still it is possible to calculate the magnification of the transmission image of the object S to be measured in an accurate manner.

If, as in the prior art technique, the object S to be measured is mounted after having first obtained the magnification by mounting a reference test specimen, then it is not possible to calculate the magnification in an accurate manner when performing measurement of the object S to be measured, since a deflection amount different to that during calibration is occurred in the measured object mounting plate 611. By contrast, since according to this embodiment the measurement pre-processing is performed in the state in which the object S to be measured is mounted and deflection has been occurred, and the magnification of the transmission image is corrected by using the relationship between the result of the measurement pre-processing, the relative position, and the magnification, accordingly it is possible to calculate the magnification of the transmission image of the object S to be measured in an accurate manner. In particular, although the error in the magnification due to the deflection of the measured object mounting plate 611 becomes great when the magnification of the transmission image is high because the distance D2 between the measured object mounting plate 611 and the X-ray source 5 is short, nevertheless, according to this embodiment, even in this type of case, it is possible to acquire the magnification at high accuracy by reducing the influence of the magnification error.

(2) The contact detection unit 41 detects contact between the measured object mounting plate 611 and the X-ray source 5 by detecting electrical contact between the contact sensitive unit 613 that is provided upon the surface of the measured object mounting plate 611 that faces the X-ray source 5 (i.e. upon its rear surface 611b) and the electrically conductive member that is provided upon the tip of the X-ray source 5 at the side of the +Z axis direction. Thus, since contact between the measured object mounting plate 611 and the X-ray source 5 is detected in an accurate manner in the state in which deflection has been occurred due to the influence of the object S to be measured, and this can be reflected in the acquisition of the magnification, accordingly this contributes to enhancement in the accuracy of the magnification that is acquired.

(3) When contact between the measured object mounting plate 611 and the X-ray source 5 is detected by the contact detection unit 41, the movement suppression unit 37 stops the driving of the X axis movement mechanism 62 and of the Y axis movement mechanism 63. Since relative movement is thereby prevented in the state in which the measured object mounting plate 611 and the X-ray source 5 are in mutual contact, accordingly it is possible to prevent damage to the measured object mounting plate 611 and to the X-ray source 5. Furthermore, it is possible to prevent the occurrence of positional deviation of the object S to be measured that is mounted upon the measured object mounting plate 611, due to the influence of vibration occurred by relative movement in the state in which the X-ray source 5 and the measured object mounting plate 611 are in mutual contact.

The X-ray apparatus 100 according to the first embodiment of the present invention as explained above may be modified in the following ways.

—Variant Embodiment #1—

Figure 7:
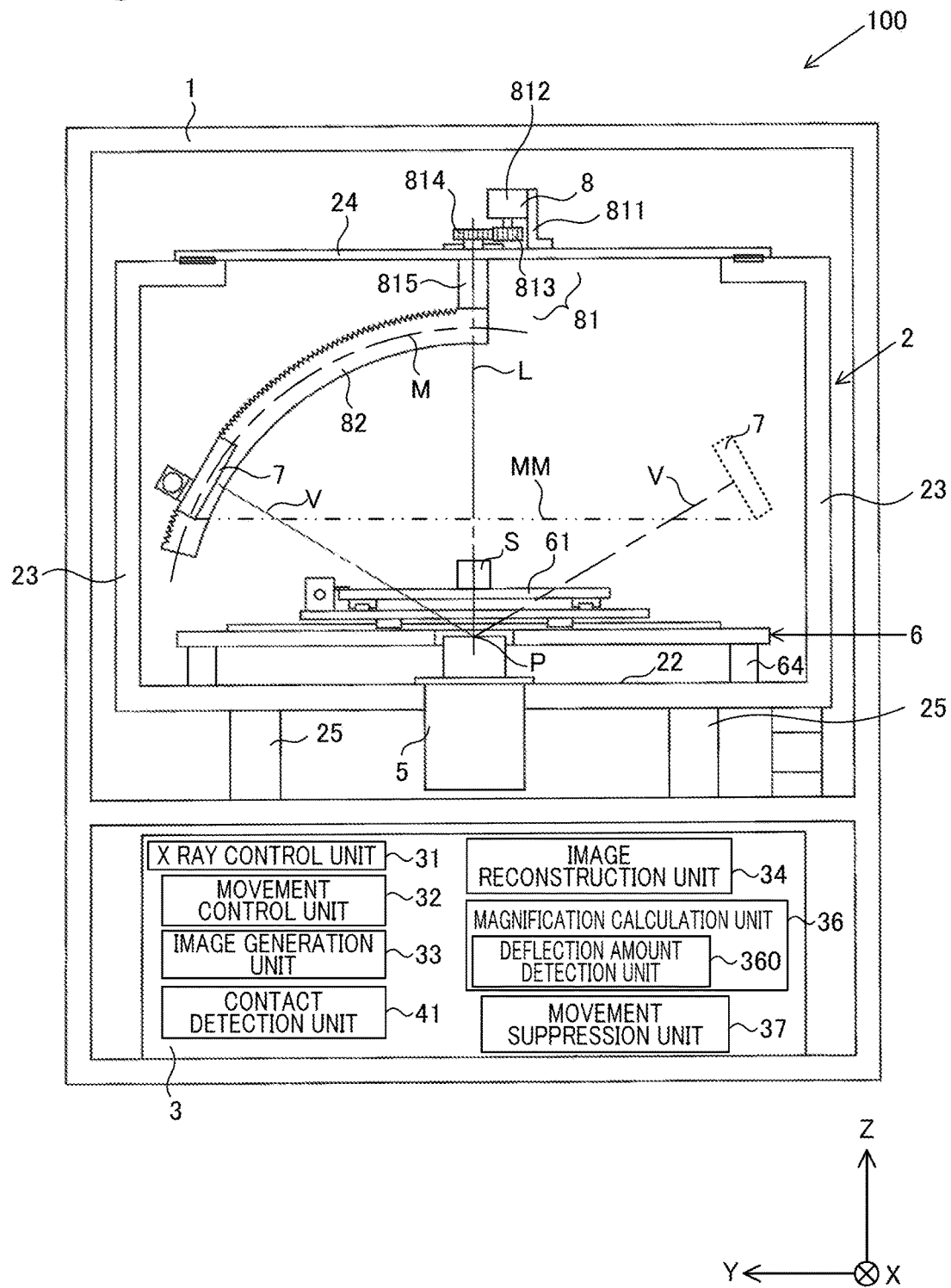
FIG. 7 is an elevation view showing the internal structure of X-ray apparatuses according to a first and a second variant embodiment.

A configuration in which no data table is provided in which the magnification of the transmission image of the object S to be measured and the relative position with respect to the X-ray source 5 are kept in mutual correspondence is also to be considered as being included as an aspect of the present invention. For example, the magnification calculation unit 36 may calculate the amount of deflection of the measured object mounting plate 611 (hereinafter termed its "deflection amount") that has been occurred by the object S to be measured having been mounted upon the measured object mounting plate 611. And the magnification calculation unit 36 calculates the magnification of the transmission image of the object S to be measured on the basis of the relationship D1/D2 described above, while taking into account this calculated deflection amount in the relative position with respect to the X-ray source 5 detected by the Z position detection unit 641. In this case, as shown in the internal structural diagram of the X-ray apparatus 100 according to this first variant embodiment shown in FIG. 7, the magnification calculation unit 36 is equipped with a deflection amount detection unit 360. As the deflection amount, this deflection amount detection unit 360 calculates the difference $\Delta z$ between the relative position z1 detected by the Z position detection unit 641 when mutual contact between the measured object mounting plate 611 and the X-ray source 5 has been detected by the contact detection unit 41, and the relative position z0 at maximum magnification that is stored in a table.

The magnification calculation unit 36 calculates the magnification of the transmission image of the object S to be measured by using this deflection amount $\Delta z$ that has been calculated by the deflection amount detection unit 360. Moreover, the magnification calculation unit 36 subtracts the deflection amount $\Delta z$ from the relative position zn of the mounting plate support unit 612 that has been detected by the Z position detection unit 641. The magnification calculation unit 36 then may calculate the magnification of the transmission image of the object S to be measured by dividing the distance D1 by the result (zn–$\Delta z$) of the subtraction described above.

—Variant Embodiment #2—

Instead of the contact sensitive unit 613 that is built as an electrically conductive member, it would also be acceptable to provide a pressure sensor upon the tip of the X-ray source 5 at the side of the +Z axis direction, and for the contact detection unit 41 to detect that the measured object mounting plate 611 and the X-ray source 5 are in mutual contact when this sensor detects the fact that pressure has been applied from the measured object mounting plate 611. Or, it would also be acceptable to provide a strain gauge to the measured object mounting plate 611, and for the contact detection unit 41 to detect contact on the basis of the amount of strain that is detected when the object S to be measured has been mounted upon the measured object mounting plate 611.

Furthermore, a configuration is also to be considered as being included as an aspect of the present invention in which, instead of detecting mutual contact between the measured object mounting plate 611 and the X-ray source 5, the fact is detected that the gap between the measured object mounting plate 611 and the X-ray source 5 has been proximate a predetermined distance or less. For example, it would be acceptable to detect such a proximity by providing an optical sensor or an electrostatic capacitance sensor upon the tip of the X-ray source 5 at the side of the +Z axis direction, and by measuring the distance between this sensor and the rear surface 611a of the measured object mounting plate 611.

—Embodiment #2—

A second embodiment of the X-ray apparatus according to the present invention will now be explained with reference to the drawings. In the following explanation, the same reference symbols will be appended to structural elements that are the same as corresponding ones in the first embodiment, and the explanation will focus upon the features of difference. Points that are not particularly explained are the same as in the first embodiment. In this second embodiment, the feature of difference from the first embodiment is that the contact detection unit 41 is not provided, but instead marks for magnification measurement are formed in order for calculation the magnification of the transmission image of the measured object mounting plate 611 to be performed, and the magnification of the transmission image of the object to be measured is calculated by using a transmission image of these marks for magnification measurement.

It should be understood that the processing explained below is performed during the measurement processing for measuring the internal structure of the object to be measured, and is not performed during the measurement pre-processing explained in connection with the first embodiment. In this second embodiment, it will be acceptable for the measurement pre-processing that was performed in the first embodiment to be executed; or, alternatively, it will also be acceptable for it not to be executed.

Figure 8:
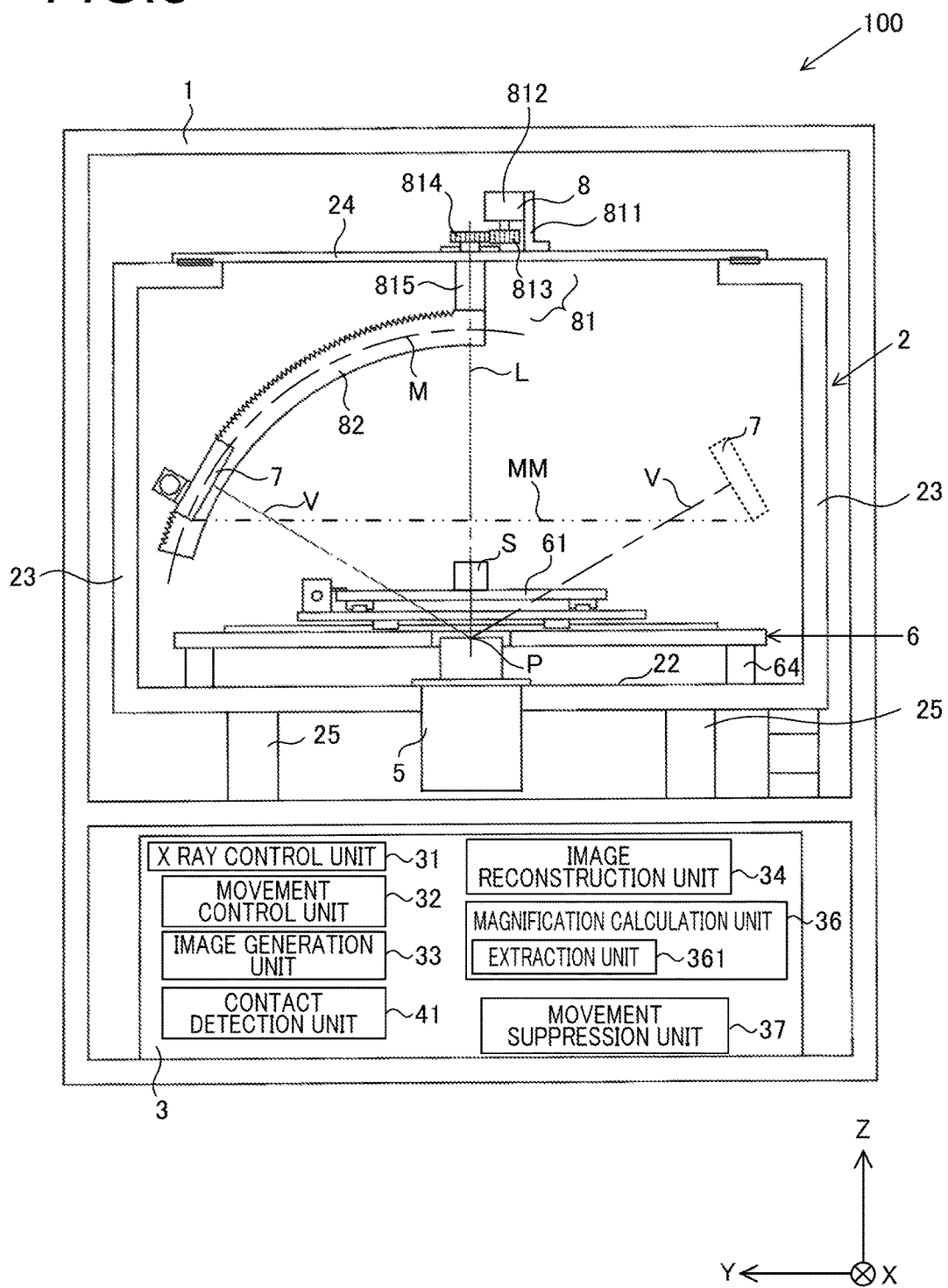
FIG. 8 is an elevation view showing the internal structure of an X-ray apparatus according to a second embodiment.
Figure 9:
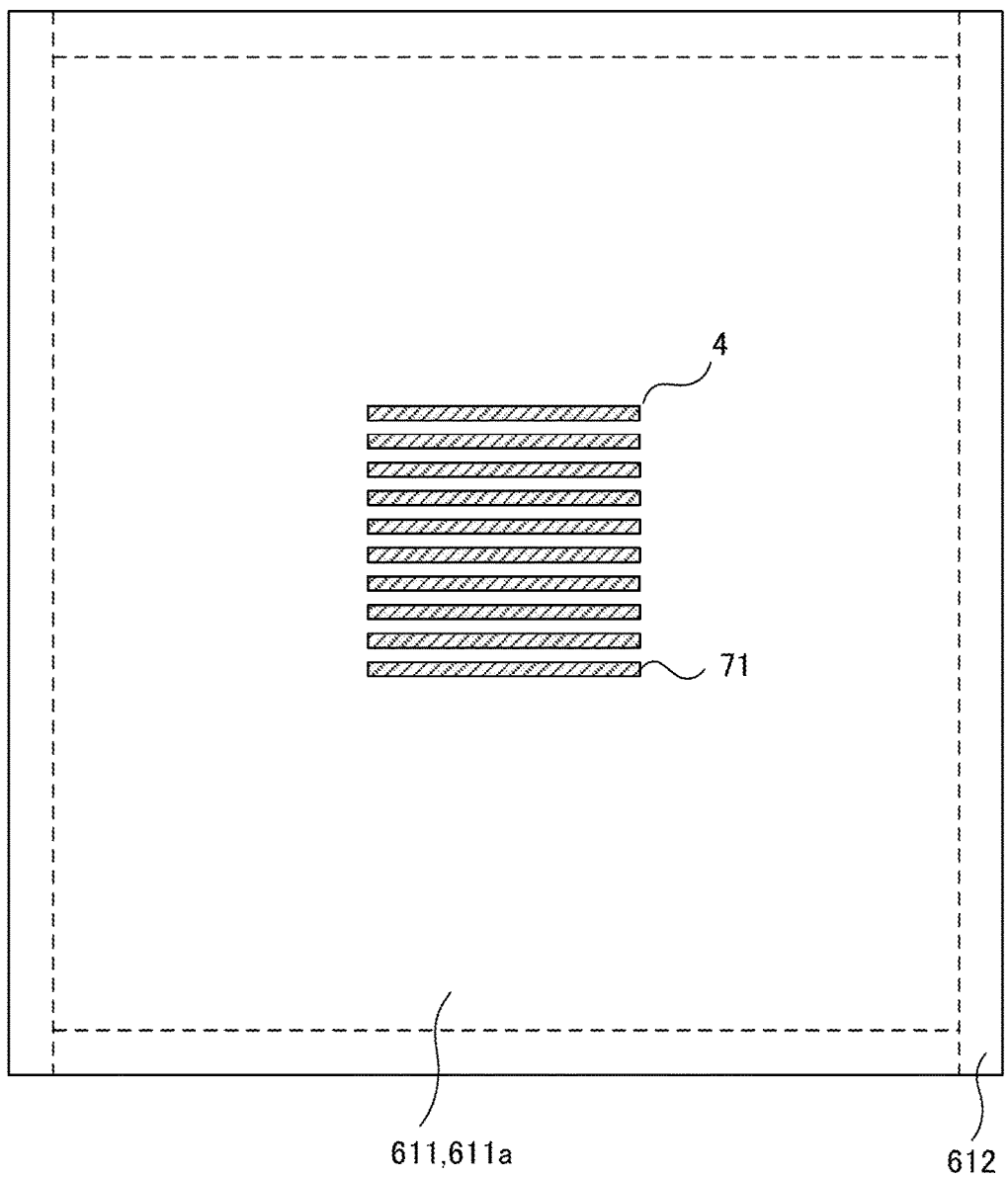
FIG. 9 is a plan view of a measured object mounting plate of this X-ray apparatus according to the second embodiment.

FIG. 8 is a figure for explanation of the internal structure of an X-ray apparatus 100 according to this second embodiment, and FIG. 9 is a plan view of a measured object mounting plate 611 thereof as seen from its +Z axis side. In this second embodiment, marks 4 for magnification measurement (refer to FIG. 9) are formed over a predetermined range upon a region at the central portion of the mounting surface 611a of the measured object mounting plate 611, for example the region where the object S to be measured is mounted (in other words, upon the region where the influence of deflection is most prominent). The marks 4 for magnification measurement are formed as a plurality of straight line segments 71 that are spaced apart at predetermined intervals and have predetermined widths. It should be understood that the marks 4 for magnification measurement are not to be considered as being limited to the shapes shown in FIG. 9; sets of marks in which a plurality of points are arranged with predetermined gaps between them, or in which indicators of various types such as alphabetic letters or the like are used, are also included as possible aspects of the present invention. A transmission image of the marks 4 for magnification measurement (hereinafter termed a "mark transmission image") is formed by those of the transmitted X-rays, among the X-rays that have been emitted from the X-ray source 5, that have passed through the straight line segments 71 being received by the X-ray detector 7. In other words, when X-rays are emitted in the state in which the object S to be measured is mounted upon the measured object mounting plate 611, a transmitted image of the object S to be measured and the mark transmission image appear upon the same projection image.

The magnification calculation unit 36 extracts the mark transmission image from the projection image, and calculates the magnification using the mark transmission image that has thus been extracted. As shown in FIG. 8, the magnification calculation unit 36 comprises an extraction unit 361 that extracts the mark transmission image from the projection image. From the transmission image of the object S to be measured and the mark transmission image, which are included in the projection image outputted from the image generation unit 33, this extraction unit 361 extracts the mark transmission image by using, for example, a pattern matching technique or the like. It should be understood that a template image that is used when extracting the mark transmission image in this manner may be stored in advance in a predetermined memory (not shown in the figures). The magnification calculation unit 36 compares a predetermined feature part from the mark transmission image that has been extracted with a feature part in the template image that corresponds to that feature part of the mark transmission image, and calculates the magnification of the feature part of the mark transmission image with respect to the feature part of the template image.

The magnification calculation processing performed by the magnification calculation unit 36 will now be explained in concrete terms with reference to FIG. 10. FIG. 10(a) is a figure schematically showing the mark transmission image 72 that is included in the projection image, and FIG. 10(b) schematically shows the template image 72. It should be understood that although, in FIG. 10(a), for the convenience of representation in the figure, only the mark transmission image 71 in the projection image is shown, actually both the mark transmission image 71 and the transmission image of the object S to be measured appear in the projection image.

As shown in FIG. 10, the magnification calculation unit 36 specifies a feature part 711 from the mark transmission image 71, and also specifies a feature part 721 from the template image 72 that corresponds to this feature part 711. In other words, the magnification calculation unit 36 specifies the width of the straight lines that form the marks 4 for magnification measured as being the feature part. And the magnification calculation unit 36 calculates both the width I1 of the feature part 711 in the projection image and also the width I2 of the feature part 721. In other words, the magnification calculation unit 36 calculates both the number of pixels that correspond to the width of the feature part 711, and also the number of pixels that correspond to the width of the feature part 721.

Using the width I1 of the feature part 711 and the width I2 of the feature part 712 that have thus been calculated, the magnification calculation unit 36 calculates the magnification of the transmission image of the object S to be measured that is included in the projection image data by calculating the ratio of the magnification of the feature part 711 of the mark transmission image 71 with respect to that of the feature part 712 of the template image 72 (in other words, by calculating I1/I2). By doing this, it is possible to calculate the magnification of the object S to be measured in an accurate manner, even if some deflection has been occurred in the measured object mounting plate 611 due to the object S to be measured having been mounted upon the measured object mounting plate 611. It should be understood that it would be acceptable for the magnification calculation unit 36 to calculate the average width I1$m$ of the width I1 of the feature part 711 of the mark transmission image 71 by measuring the width at a plurality of different spots in the left and right direction, and to perform the calculation of the magnification by using this average width I1$m$ (in other words, by calculating I1$m$/I2). Even if the marks 4 are locally distorted, it is not likely that much error will be experienced due to that influence.

In this embodiment as well, in a similar manner to the case in the first embodiment, a reconstructed image is generated by the image reconstruction unit 34. Since, as described above, the projection image includes both the transmission image of the object S to be measured and also the mark transmission image, accordingly both the object S to be measured and also the marks 4 for magnification measurement are included in the reconstructed image that is generated. It should be understood that it would also be acceptable for the magnification calculation object 36 to eliminate the mark transmission image from the projection image, so that only the object S to be measured is included in the reconstructed image.

Figure 11:
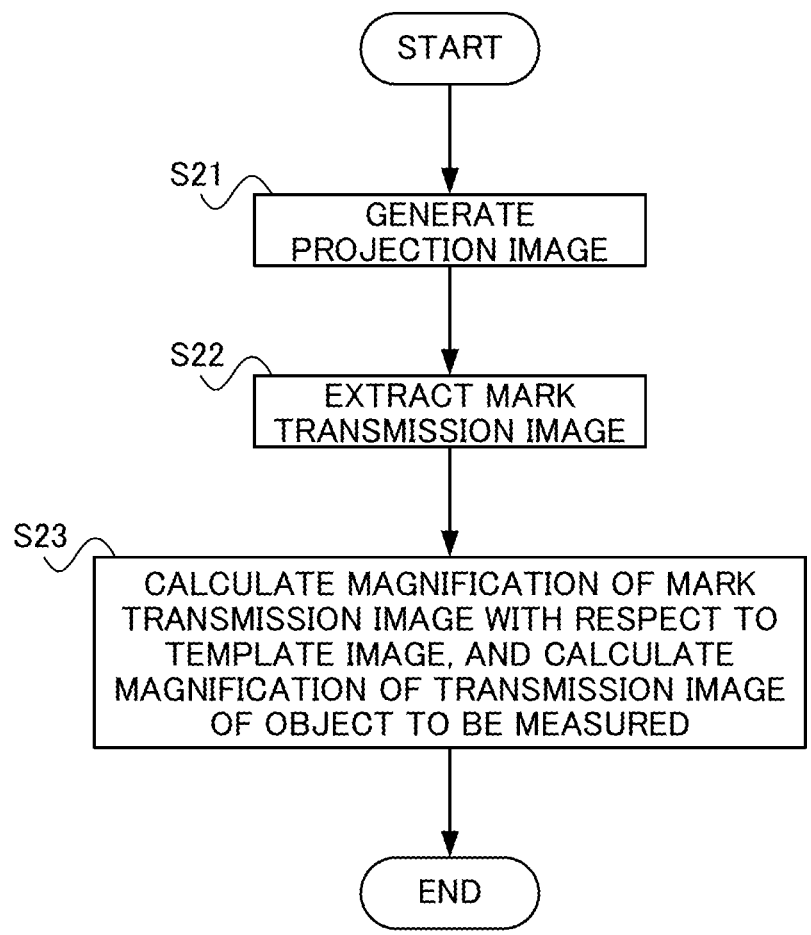
FIG. 11 is a flow chart for explanation of the operation of processing for magnification calculation, according to the second embodiment.

The processing described above for calculation of the magnification of the object S to be measured will now be explained with reference to the flow chart of FIG. 11. A program is executed by the control device 3 for performing the processing shown in the flow chart of FIG. 11. This program is stored in a memory (not shown in the figures), and is started and executed by the control device 3 when the object S to be measured is mounted upon the measured object mounting plate 611, and actuation for starting operation is performed by the user.

First in step S21 the image generation unit 33 generates the projection image data, and then the flow of control proceeds to step S22. In step S22, the extraction unit 361 of the magnification calculation unit 36 extracts the mark transmission image from the transmission image of the object S to be measured and the mark transmission image that are included in the projection image, and then the flow of control proceeds to step S23. In step S23, the magnification of the transmission image of the object S to be measured is calculated by calculating the magnification of the mark transmission image with respect to that of the template image 72, and then this processing terminates.

It should be understood that, in this embodiment, the contact detection unit 41 decides that the measured object mounting plate 611 and the X-ray source 5 are in mutual contact when the magnification of the transmission image of the object S to be measured calculated by the magnification calculation unit 36 becomes the maximum magnification. Or, the contact detection unit 41 may decide that the measured object mounting plate 611 and the X-ray source 5 are in mutual contact via the fact that, while the mounting plate support unit 612 was being moved by the Z axis movement mechanism 64, change of the magnification of the transmission image of the object S to be measured as calculated by the magnification calculation unit 36 ceased to occur. If it has been decided by the contact detection unit 41 that contact between the measured object mounting plate 611 and the X-ray source 5 is taking place, then, in a similar manner to the case with the first embodiment, the movement suppression unit 37 stops (i.e. suppresses) the driving of the X axis movement mechanism 62 and the Y axis movement mechanism 63.

According to the X-ray apparatus according to the second embodiment of the present invention described above, the following beneficial operational effects may be obtained.

(1) The marks 4 for magnification measurement are formed upon the measured object mounting plate 611, and the magnification calculation unit 36 calculates the magnification of the transmission image of the object S to be measured on the basis of the mark transmission image, among the transmission image of the object S to be measured and the mark transmission image that are included in the projection image generated by the image generation unit 33. Accordingly, it is still possible to calculate the magnification of the transmission image of the object S to be measured in an accurate manner, even if a deflection has been occurred in the measured object mounting plate 611 corresponding to the weight of the object S to be measured.

(2) The marks 4 for magnification measurement are formed upon the mounting surface 611*a* of the measured object mounting plate 611. Since, due to this, the distance from the X-ray source 5 to the marks 4 for magnification measurement becomes substantially equal to the distance from the X-ray source 5 to the object S to be measured, accordingly it is possible to enhance the accuracy when calculating the magnification using the mark transmission image.

(3) The extraction unit 361 extracts the mark transmission image from the transmission image of the object S to be measured and the mark transmission image, and the magnification calculation unit 36 calculates the magnification of the transmission image of the object S to be measured on the basis of the mark transmission image that has thus been extracted by the extraction unit 361. Accordingly, it is possible to calculate the magnification of the transmission image of the object S to be measured at high accuracy.

The X-ray apparatus 100 according to the second embodiment of the present invention as explained above may be varied in the following ways.

—Variant Embodiment #3—

Figure 12:
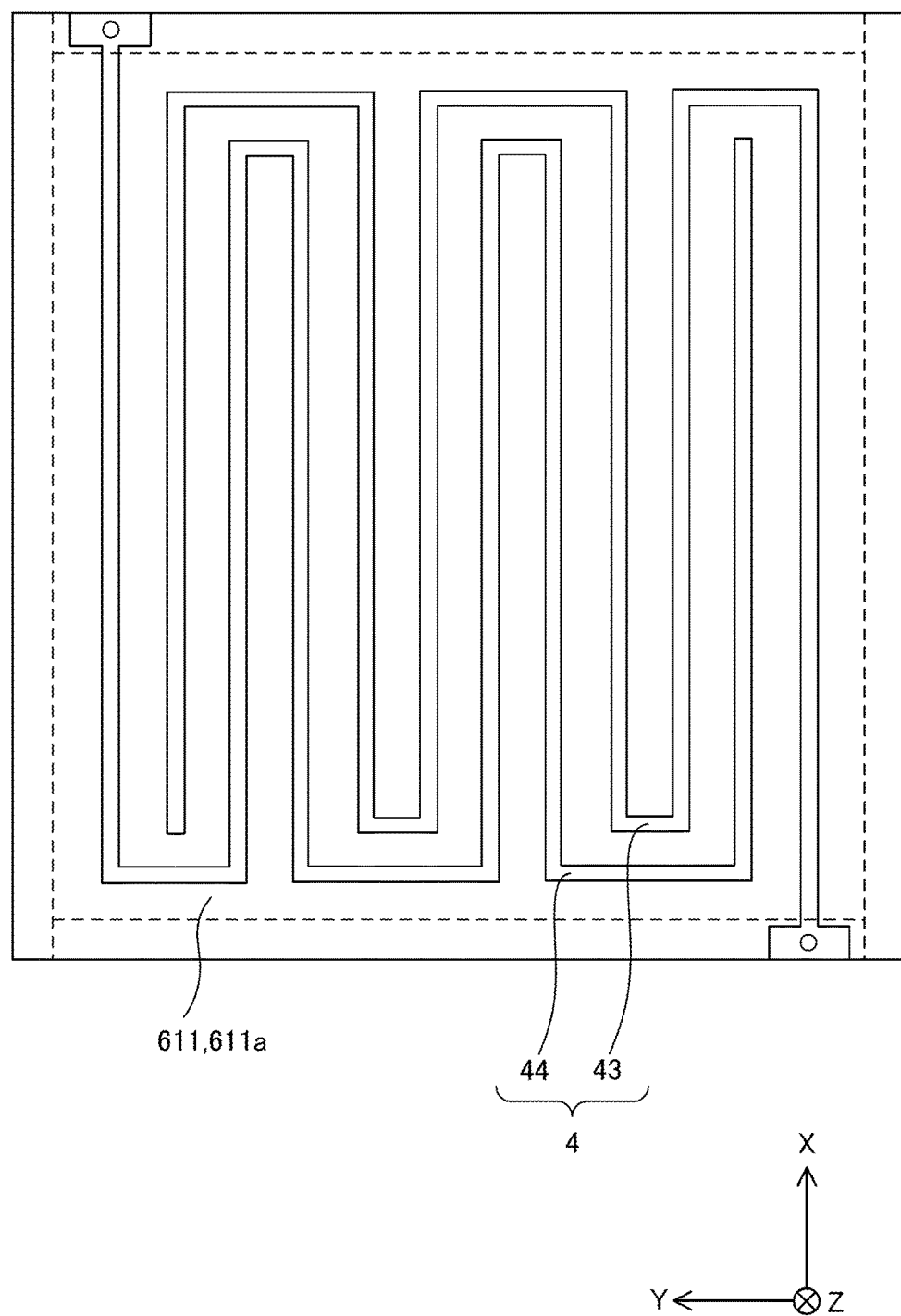
FIG. 12 is a figure for explanation of an example of a mark for magnification measurement, according to a third variant embodiment.

It would also be acceptable to form the marks 4 for magnification measurement as electrically conductive members upon the rear surface 611*b* of the measured object mounting plate 611. In other words, the marks 4 for magnification measurement may also serve as the contact sensitive unit of the first embodiment. An example of the marks 4 for magnification measurement according to this fourth variant embodiment is shown in FIG. 12. FIG. 12 is a figure showing the measured object mounting plate 611 as seen from the side of its rear surface 611*b* (i.e. from the −Z axis side). The marks 4 for magnification measurement consist of a first mark 43 and a second mark 44. Each of the first mark 43 and the second mark 44 is made as an electrically conductive member.

When the measured object mounting plate 611 and the X-ray source 5 are in mutual contact, since the tip of the X-ray source 5 at the side of +Z axis direction is touched by the electrically conductive members, accordingly the first mark 43 and the second mark 44 are electrically connected together. The contact detection unit 41 detects the value of resistance between the first mark 43 and the second mark 44, and determines that the measured object mounting plate 611 and the X-ray source 5 are in mutual contact when this resistance value is substantially zero [Ω], while determining that the measured object mounting plate 611 and the X-ray source 5 are not in mutual contact when this resistance value is substantially infinite [Ω]. If it has been determined that the X-ray source 5 and the measured object mounting plate 611 are in mutual contact, then the movement suppression unit 37 stops the driving of the X axis movement mechanism 62 and Y axis movement mechanism 63, and thereby causes the movement of the measured object mounting plate 611 in the X-Y plane to stop.

—Variant Embodiment #4—

If the weight of the object S to be measured is great and the deflection occurred in the measured object mounting plate 611 is large, then the marks 4 for magnification measurement undergo high deformation (i.e. distortion). Accordingly, for example, the amount of deformation of the marks 4 for magnification measurement with respect to the weight of the object S to be measured may be measured in advance by experiment or the like, and may be stored in a memory (not shown in the figures). And, for example by providing a weight sensor or the like to the mounting table 61, before starting measurement of the internal structure of the object S to be measured, the weight of the object S to be measured is acquired in advance. It should be understood that it would also be acceptable to acquire the weight of the object S to be measured on the basis of its design information. The magnification measurement unit 36 corrects the width I2 of the feature part 721 of the template image 72 by using this information related to weight that has thus been acquired. And the magnification measurement unit 36 calculates the ratio of the magnification of the feature part 711 of the mark transmission image 71 with respect to that of the feature part 712 of the template image 72 by using the width I2 of the feature part 721 after this correction, and the width I1 or the average width I1$m$ of the feature part of the mark transmission image 71, and then calculates the magnification in a similar manner to the case for the second embodiment, described above.

—Embodiment #3—

A third embodiment of the X-ray apparatus according to the present invention will now be explained with reference to the drawings. In the following explanation, the same reference symbols will be appended to structural elements that are the same as corresponding ones in the first and second embodiments, and the explanation will focus upon the features of difference. Points that are not particularly explained are the same as in the first and second embodiments. In this embodiment, the difference from the first and the second embodiments is the feature that the system changes over between performing calculation of the magnification of the object to be measured by using the relative position as detected by the Z position detection unit, and performing calculation of the magnification of the object to be measured by using a transmission image of marks for magnification measurement.

It should be understood that the processing explained below is performed during the measurement processing for measuring the internal structure of the object to be measured, and is not performed during the measurement pre-processing explained in connection with the first embodiment. In this third embodiment, it will be acceptable for the measurement pre-processing that was performed in the first embodiment to be executed; or, alternatively, it will also be acceptable for it not to be executed.

Figure 13:
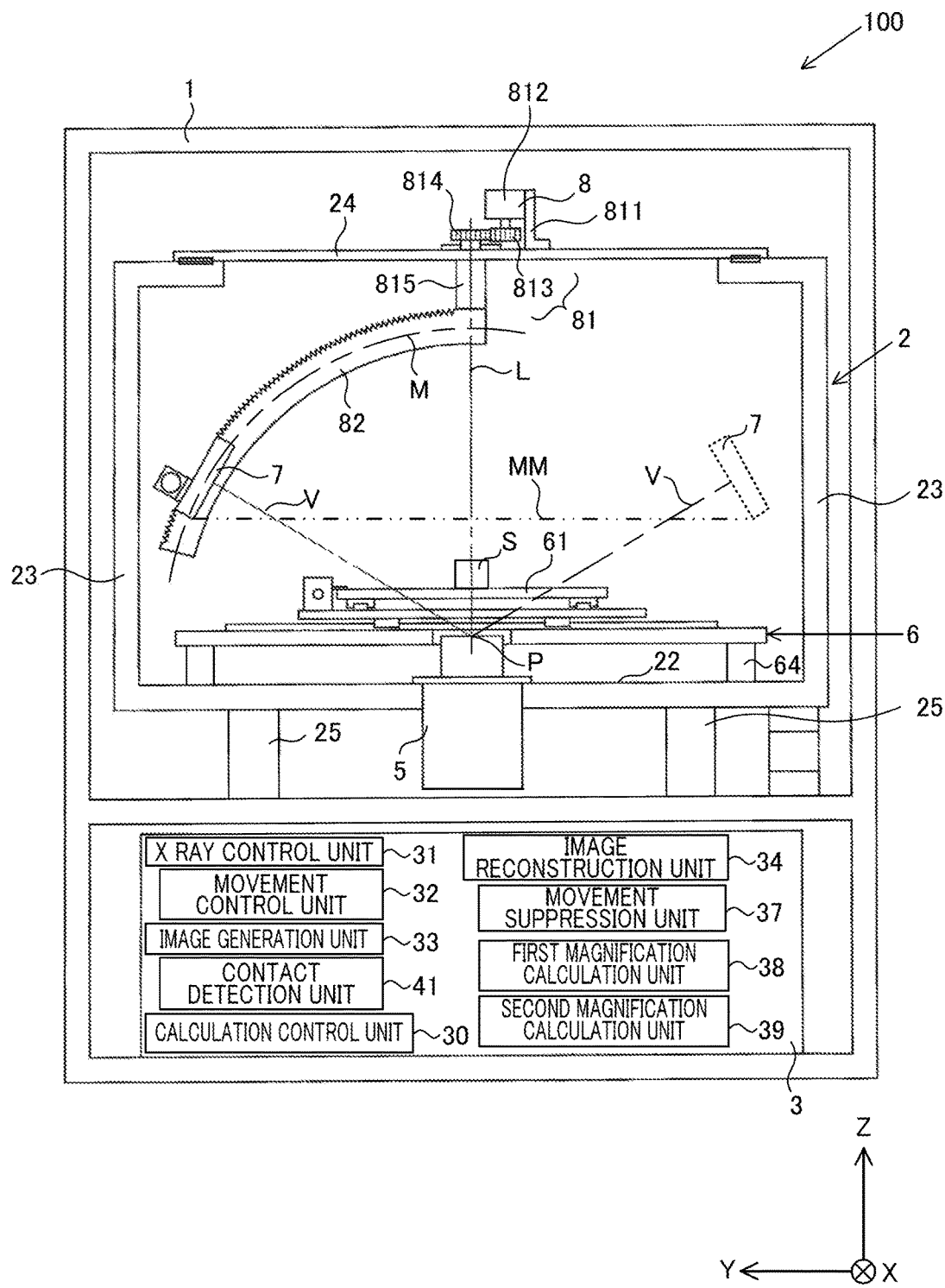
FIG. 13 is an elevation view showing the internal structure of an X-ray apparatus according to a third embodiment.

The structure of an X-ray apparatus 100 according to this third embodiment is shown in FIG. 13. In this X-ray apparatus 100 of this third embodiment, marks 4 for magnification measurement (refer to FIG. 9) as explained in connection with the second embodiment are formed upon the mounting surface 611a of the measured object mounting plate 611, and a contact sensitive unit 613 is provided upon its rear surface 611b. And a control device 3 comprises an X-ray control unit 31, a movement control unit 32, an image generation unit 33, an image reconstruction unit 34, a movement suppression unit 37, a first magnification calculation unit 38, a second magnification calculation unit 39, a calculation control unit 30, and a contact detection unit 41.

In a similar manner to the case with the magnification calculation unit 36 of the first embodiment, the first magnification calculation unit 38 calculates the magnification of the transmission image of the object S to be measured on the basis of the relative position of the mounting plate support unit 612 as detected by the Z position detection unit 641. And, in a similar manner to the case with the magnification calculation unit 36 of the second embodiment, the second magnification calculation unit 39 calculates the magnification of the transmission image of the object S to be measured in the projection image by employing the mark transmission image, among the transmission image of the object S to be measured and the mark transmission image that are included in the projection image.

According to the relative position as detected by the Z position detection unit 641 when the mounting plate support unit 612 has been moved to the target position, the calculation control unit 30 causes one of the first magnification calculation unit 38 and the second magnification calculation unit 39 to perform calculation of the magnification of the transmission image of the object S to be measured. For example, if the relative position with respect to the X-ray source 5 is large, in other words if the distance from the X-ray source 5 to the mounting plate support unit 612 is comparatively great, and the magnification of the transmission image of the object S to be measured is comparatively small, then the error in the magnification is small. On the other hand, if the distance from the X-ray source 5 to the mounting plate support unit 612 is comparatively small, and the magnification of the transmission image of the object S to be measured is comparatively great, then the error in the magnification is large.

In this embodiment, for example, the relative position z3 with respect to the X-ray source 5 shown in FIG. 5 may be set as the changeover position, and then, if the relative position with respect to the X-ray source 5 as detected by the Z position detection unit 641 is greater than this changeover position, in other words if the distance from the X-ray source 5 to the mounting plate support unit 612 is large, then the calculation control unit 30 determines that the influence that the deflection occurred by mounting of the object S to be measured exerts upon the magnification of the transmission image is small. If the magnification of the transmission image of the object S to be measured is small, then the calculation control unit 30 calculates the magnification of the transmission image of the object S to be measured with the first magnification calculation unit 38 by employing the relative position with respect to the X-ray source 5 as detected by the Z position detection unit 641. If the relative position with respect to the X-ray source 5 as detected by the Z position detection unit 641 is smaller than the changeover position, in other words if the distance from the X-ray source 5 to the mounting plate support unit 612 is small, then the calculation control unit 30 determines that the influence that the deflection occurred by mounting of the object S to be measured exerts upon the magnification of the transmission image is large. And, if the magnification of the transmission image of the object S to be measured is large, then the calculation control unit 30 calculates the magnification of the transmission image of the object S to be measured with the second magnification calculation unit 39 by employing the transmission image of the marks 4 for magnification measurement (i.e. the mark transmission image) included in the projection image outputted from the image generation unit 33.

Figure 14:
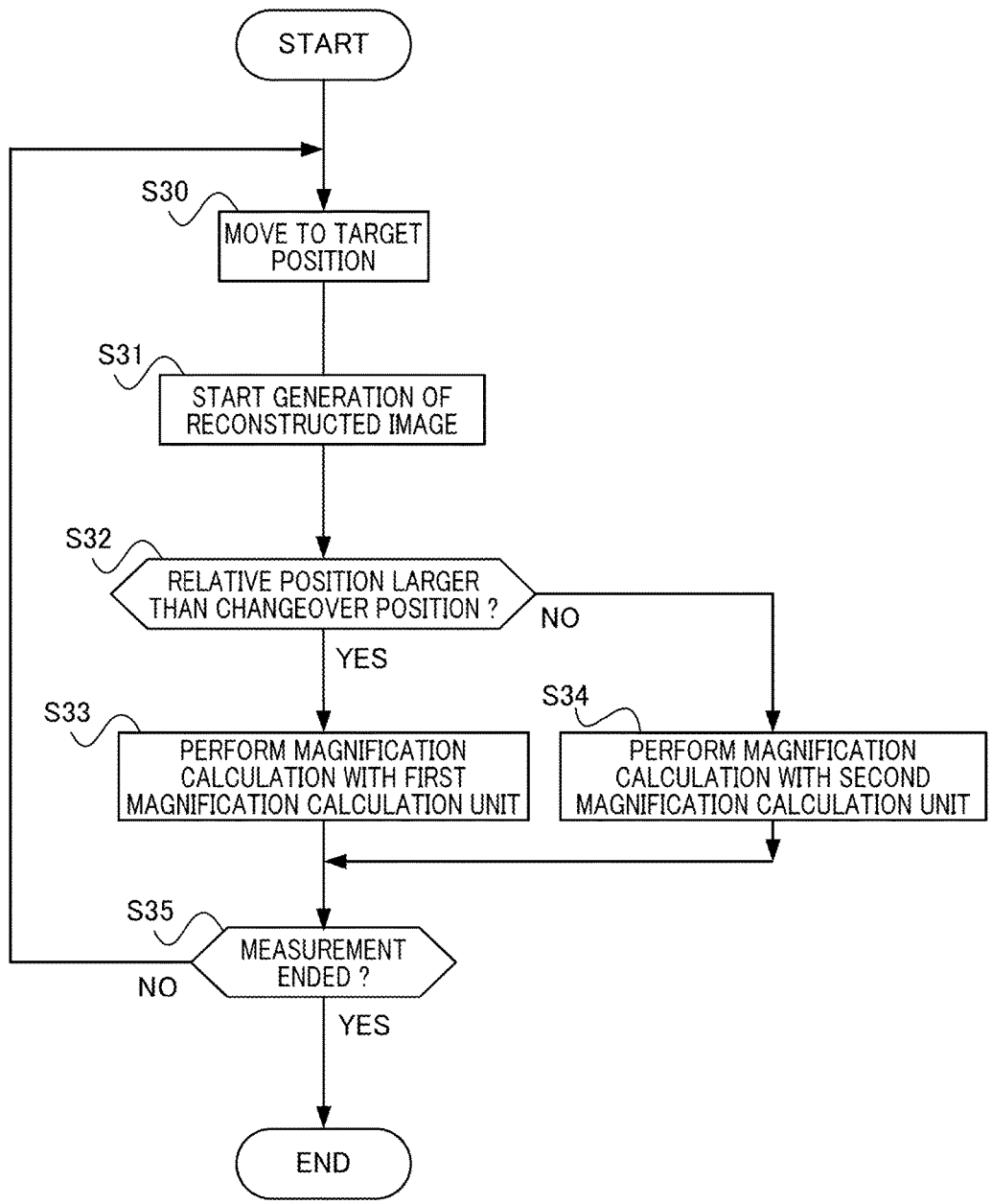
FIG. 14 is a flow chart for explanation of the operation of the X-ray apparatus according to the third embodiment.

The operation of the X-ray apparatus 100 will now be explained with reference to the flow chart of FIG. 14. A program is executed by the control device 3 for performing the processing shown in the flow chart of FIG. 14. This program is stored in a memory (not shown in the figures), and is started and executed by the control device 3 when the object S to be measured is mounted upon the measured object mounting plate 611, and actuation for starting operation is performed by the user.

In step S30 the Z axis movement mechanism 64 is driven, and, in the state in which the object S to be measured is mounted upon the measured object mounting plate 611, the mounting plate support unit 612 is moved to a predetermined target position in the Z axis direction, and then the flow of control proceeds to step S31. In step S31, X-rays are emitted from the X-ray source 5 and the generation of a reconstructed image is started on the basis of the electrical signals outputted from the X-ray detector 7, and then the flow of control proceeds to step S32. In step S32, a decision is made as to whether or not, at the target position, the relative position with respect to the X-ray source 5 as detected by the Z position detection unit 641 is greater than the changeover position (i.e. the relative position z3). If the relative position with respect to the X-ray source 5 that has been detected is greater than the changeover position, then an affirmative decision is reached in step S32 and the flow of control proceeds to step S33. But if the relative position with respect to the X-ray source 5 that has been detected is smaller than the changeover position, then a negative decision is reached in step S32 and the flow of control is transferred to step S34.

In step S33, the calculation control unit 30 performs magnification calculation with the first magnification calculation unit 38, and then the flow of control proceeds to step S35. And, in step S34, the calculation control unit 30 performs magnification calculation with the second magnification calculation unit 39, and then the flow of control proceeds to step S35. In step S35, a decision is made as to whether or not measurement has ended. If actuation to terminate measurement of the internal structure of the object S to be measured has been performed by the user, then an affirmative decision is reached in step S35 and this processing terminates. But if actuation to terminate measurement of the internal structure of the object S to be measured has not been performed by the user, then a negative decision is reached in step S35 and the flow of control returns to step S30.

According to the X-ray apparatus according to the third embodiment of the present invention described above, the following beneficial operational effects may be obtained.

The calculation control unit 30 causes either one of the first magnification calculation unit 38 and the second magnification calculation unit 39 to calculate the magnification of the object S to be measured. The first magnification calculation unit 38 calculates the magnification of the transmission image of the object S to be measured on the basis of the relative position of the mounting plate support unit 612 with respect to the X-ray source 5 as detected by the Z position detection unit 641. And the second magnification calculation unit 39 calculates the magnification of the object S to be measured on the basis of the transmission image of the marks 4 for magnification measurement that are formed upon the measured object mounting plate 611. When the mounting plate support unit 612 has been moved to the target position, if its relative position with respect to the X-ray source 5 as detected by the Z position detection unit 641 is greater than the changeover position, in other words if the magnification of the transmission image of the object S to be measured is small, then the calculation control unit 30 calculates the magnification of the transmission image of the object S to be measured with the first magnification calculation unit 38. But if the relative position with respect to the X-ray source 5 as detected by the Z position detection unit 641 is smaller than the changeover position, in other words if the magnification of the transmission image of the object S to be measured is large, then the calculation control unit 30 calculates the magnification of the transmission image of the object S to be measured with the second magnification calculation unit 39. Accordingly, if the magnification of the transmission image of the object S to be measured is large, and the error in the magnification due to deflection occurred in the measured object mounting plate 611 is large, then, by employing the projection image, it becomes possible to calculate the magnification at high accuracy even though an influence is being experienced due to deflection; whereas, if the magnification of the transmission image of the object S to be measured is small, and the error in the magnification due to deflection occurred in the measured object mounting plate 611 is small, then it becomes possible to reduce the load required for processing, since the calculation of the magnification is performed while not employing the projection image.

The X-ray apparatus 100 according to the third embodiment of the present invention explained above may be varied as will now be described. It should be understood that configurations in which the third and fourth variant embodiments described above are applied to the X-ray apparatus 100 of the third embodiment are also to be considered as included in the scope of the present invention.

Instead of the calculation control unit 30 calculating the magnification of the transmission image of the object S to be measured by using either the first magnification control unit 38 or the second magnification control unit 39 according to the relative position as detected by the Z position detection unit 641 and the magnitude of the threshold value, a system in which the calculation control unit 30 performs the following control is also to be considered as coming within the scope of the present invention. That is to say, irrespective of the result detected by the Z position detection unit 641 when the mounting plate support unit 621 has been moved to the target position, the calculation control unit 30 calculates the magnification of the transmission image of the object S to be measured both with the first magnification control unit 38 and with the second magnification control unit 39. And the calculation control unit 30 calculates the difference between the magnification calculated by the first magnification calculation unit 38 and the magnification calculated by the second magnification calculation unit 39. If the difference between the two of them is small, then the error in the magnification of the transmission image of the object S to be measured caused by the deflection occurred in the measured object mounting plate 611 can be considered as being small, and the calculation control unit 30 selects the magnification that has been calculated by the first magnification calculation unit 38 on the basis of the relative position with respect to the X-ray source 5 as detected by the Z position detection unit 641 as being the magnification of the transmission image of the object S to be measured. On the other hand, if the difference is large, then the error in the magnification of the transmission image of the object S to be measured caused by the deflection occurred in the measured object mounting plate 611 must be considered as being large, and the calculation control unit 30 selects the magnification that has been calculated by the second magnification calculation unit 39 by using the mark transmission image as being the magnification of the transmission image of the object S to be measured.

—Embodiment #4—

A structure manufacturing system according to an embodiment of the present invention will now be explained with reference to the drawings. The structure manufacturing system of this embodiment may, for example, be used for manufacturing a molded component such as a door portion, an engine portion, or a gear portion of an automobile, or an electronic component that incorporates a circuit board.

Figure 15:
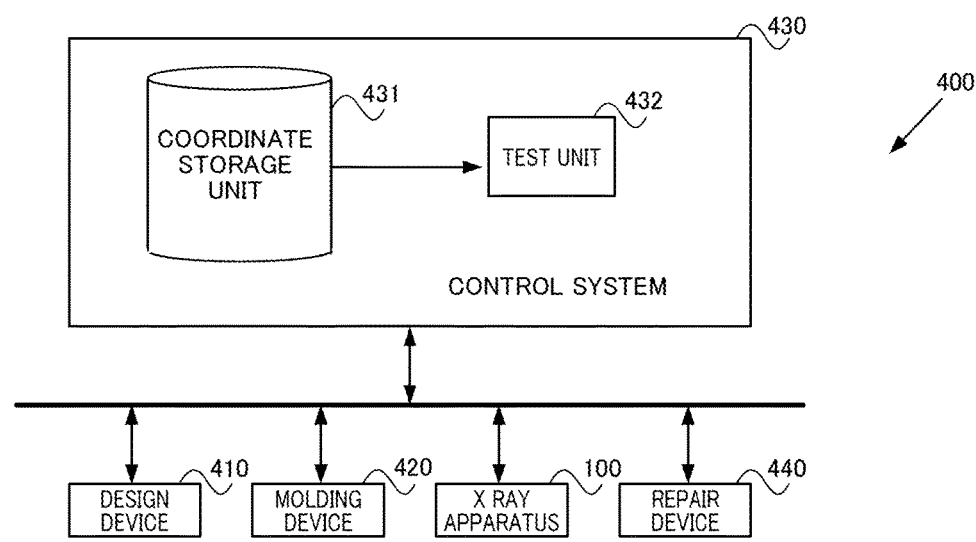
FIG. 15 is a block diagram showing the structure of a structure manufacturing system according to a fourth embodiment.

FIG. 15 is a block diagram showing an example of the structure of a structure manufacturing system 400 according to this embodiment. This structure manufacturing system 400 comprises an X-ray apparatus 100 of the type explained above in relation to the first through the third embodiments, a design device 410, a molding device 420, a control system 430, and a repair device 440.

The design device 410 is a device that the user employs when creating design information related to the shape of a structure, and performs design processing for creating and storing design information. Such design information is information that specifies the coordinates of positions upon the structure. The design information is outputted to the molding device 420 and to a control system 430 that will be described hereinafter. The molding device 420 constructs a structure by using the design information created by the design device 410, and molds that structure by performing molding processing. Any case in which the molding device 420 performs at least one of a lamination process which is representative of 3D printing techniques, a casting process, a forging process, and a cutting process is to be considered as being an aspect of the present invention.

The X-ray apparatus 100 performs measurement processing in order to measure the shape of a structure that has been molded by the molding device 420. The X-ray apparatus 100 outputs to the control system 430 information (subsequently termed "shape information") specifying coordinates on the structure that are results of measuring the structure. The control system 430 comprises a coordinate storage unit 431 and a test unit 432. The coordinate storage unit 431 stores the design information created by the design device 410 described above.

The test unit 432 makes a decision as to whether or not the structure that has been molded by the molding device 420 has been molded according to the design information created by the design device 410. To put this in another manner, the test unit 432 makes a decision as to whether or not the structure that has been molded is a satisfactory product. In this case, the test unit 432 reads out the design information stored in the coordinate storage unit 431, and performs testing processing for comparing this design information with the shape information that has been inputted from the X-ray apparatus 100. As this testing processing, for example, the test unit 432 may compare together the coordinates specified in the design information and coordinates specified by the corresponding shape information, and may determine that this product is a satisfactory product that has been molded according to the design information if the result of this testing processing shows that the coordinates in the design information and the coordinates in the shape information agree with one another. But if the coordinates in the design information and the corresponding coordinates in the shape information do not agree with one another, then the test unit 432 decides whether or not the differences between the coordinates are within predetermined ranges, and, if they are within those predetermined ranges, decides that this product is an unsatisfactory product that can be repaired.

If it has been decided that this product is an unsatisfactory product that can be repaired, then the test unit 432 outputs to the repair device 440 repair information that specifies the bad portions and the amounts of repair they need. The bad portions are the coordinates in the shape information that do not agree with the coordinates in the design information, and the amounts of repair are the differences at the bad portions between the coordinates in the design information and the coordinates in the shape information. And, on the basis of this repair information that has thus been inputted, the repair device 440 performs repair processing to perform re-processing at the bad portions of the structure. In this repair processing, the repair device 440 performs similar processing to the molding processing that was performed by the molding device 420, for a second time.

Figure 16:
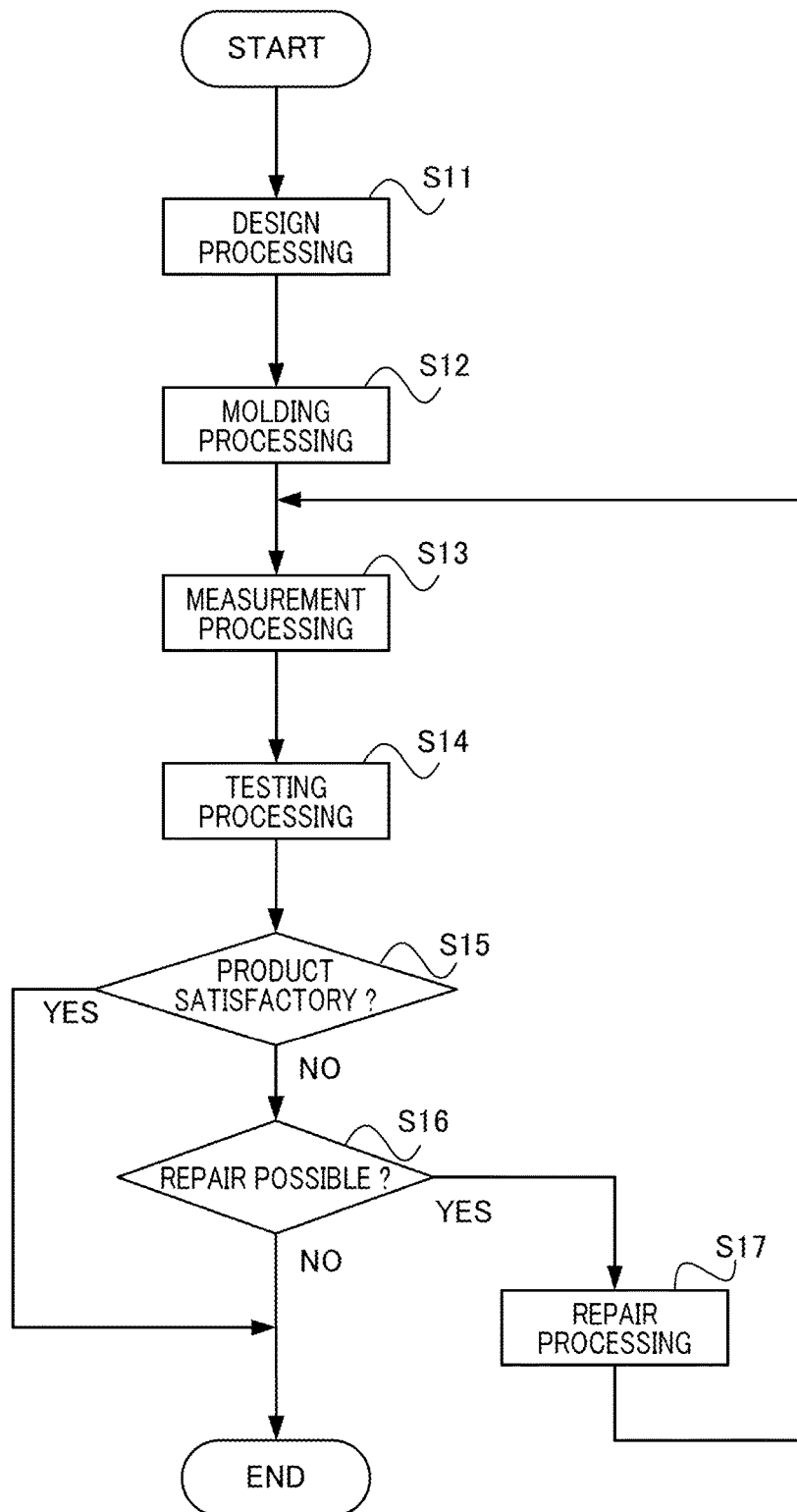
FIG. 16 is a flow chart for explanation of the operation of this structure manufacturing system according to the fourth embodiment.

The processing performed by the structure manufacturing system 400 will now be explained with reference to the flow chart shown in FIG. 16.

In step S11, the design device 410 is employed by the user while performing design of a structure, and creates and stores design information related to the shape of the structure produced by this design processing, and then the flow of control proceeds to step S12. It should be understood that the design device 410 is not limited only to design information that is produced by the design device; a case in which the design information is already in existence and this design information is acquired by being inputted is also to be considered as being one aspect of the present invention. In step S12, the molding device 420 manufactures and molds a structure on the basis of the design information by molding processing, and then the flow of control proceeds to step S13. In step S13, the X-ray apparatus 100 performs measurement processing to measure the shape of the structure and outputs this shape information, and then the flow of control proceeds to step S14.

In step S14, the test unit 432 performs testing processing to compare together the design information created by the design device 410 and the shape information measured and outputted by the X-ray apparatus 100, and then the flow of control proceeds to step S15. In step S15, on the basis of the result of testing processing, the test unit 432 makes a decision as to whether or not the structure that has been molded by the molding device 420 is a satisfactory product. If this structure is a satisfactory product, in other words if the coordinates in the design information and the coordinates in the shape information agree with one another, then an affirmative decision is reached in step S15 and processing terminates. But if the structure is not a satisfactory product, in other words if the coordinates in the design information and the coordinates in the shape information do not agree with one another, or if some coordinates that are not present in the design information are detected, then a negative decision is reached in step S15 and the flow of control proceeds to step S16.

In step S16, the test unit 432 makes a decision as to whether or not the bad portion or portions in the structure can be repaired. If the bad portions are not repairable, in other words if, at the bad portions, the differences between the coordinates in the design information and the coordinates in the shape information are outside the predetermined ranges, then a negative decision is reached in step S16 and processing terminates. But if the bad portions are repairable, in other words if, at the bad portions, the differences between the coordinates in the design information and the coordinates in the shape information are within the predetermined ranges, then an affirmative decision is reached in step S16 and the flow of control proceeds to step S17. In this case, the test unit 432 outputs repair information to the repair device 440. In step S17, the repair device 440 performs repair processing upon the structure on the basis of this repair information that has been inputted, and then the flow of control returns to step S13. It should be understood that, in the repair processing, as described above, the repair device 440 re-performs similar processing to the molding processing that the molding device 420 performed.

According to this structure manufacturing system 400 according to the fourth embodiment of the present invention described above, the following beneficial operational effects may be obtained.

(1) The X-ray apparatus 100 of the structure manufacturing system 400 performs measurement processing to acquire shape information about the structure that has been manufactured by the molding device 420 on the basis of the design processing performed by the design device 410, and the test unit 432 of the control system 430 performs testing processing to compare the shape information acquired by this measurement processing with the design information that was created in the design processing. Accordingly a contribution is made to management of structure product quality, since it is possible to acquire information about testing for defects in the structure and about the interior of the structure by non-destructive testing, and since it is possible to determine whether or not this structure is a satisfactory product that has been manufactured by following the design information.

(2) It is arranged for the repair device 440 perform repair processing, upon the basis of the result of comparison by the testing processing, so as to perform the molding processing upon the structure again. Accordingly, a contribution is made to manufacture of a structure of high product quality that is close to the design information, since it is possible to perform processing upon the structure that is similar to re-molding processing, if there is some portion of the structure that is not of good quality and that can be repaired.

Variations of the following type are also to be considered as coming within the scope of the present invention, and, moreover, it would also be possible to combine one or a plurality of these variant embodiments with one of the embodiments described above.

(1) A device having a construction in which the mounting unit 6 is disposed on the −Z axis side with respect to the X-ray source 5, the X-ray detector 7 is disposed on the −Z axis side with respect to the mounting unit 6, and X-rays are irradiated upon the object S to be measured that is mounted upon the mounting unit 6 from the +Z axis side, is also to be considered as being an aspect of the present invention.

(2) The present invention is not to be considered as being limited to a structure in which the mounting unit 6 moves in the Z-axis direction; a structure in which the X-ray source 5 or the X-ray detector 7 moves in the Z axis direction also comes within the scope of a possible aspect of the present invention.

The present invention is not to be considered as being limited to the embodiments described above; provided that the particular features of the present invention are not departed from, other implementations that are considered to come within the scope of the technical concept of the present invention are also included within the range of the present invention.

REFERENCE SIGNS LIST

3: control device, 4: mark for magnification measurement, 5: X-ray source, 6: mounting unit, 7: X-ray detector, 30: calculation control unit, 31: X-ray control unit, 32: movement control unit, 33: image generation unit, 34: image reconstruction unit, 36: magnification calculation unit, 37: movement suppression unit, 38: first magnification calculation unit, 39: second magnification calculation unit, 41: contact detection unit, 61: mounting table, 62: X axis movement mechanism, 63: Y axis movement mechanism, 64: Z axis movement mechanism, 100: X-ray apparatus, 400: structure manufacturing system, 410: design device, 420: molding device, 430: control system, 432: test unit, 440: repair device, 360: deflection amount detection unit, 361: extraction unit, 611: measured object mounting plate, 612: mounting plate support unit, 613: contact sensitive unit.

The invention claimed is:

1. An X-ray apparatus, comprising:
a mounting unit upon which an object to be measured is mounted;
an X-ray generator that irradiates X-rays, from above the mounting unit or from below the mounting unit, to the object to be measured that is mounted upon the mounting unit;
an X-ray detector that acquires a transmission image of the object to be measured that is being irradiated by the X-rays, in a state in which a magnification of the transmission image of the object to be measured is set; and
a calculator that calculates the magnification of the transmission image of the object to be measured that is acquired by the X ray detector when the object to be measured is mounted upon the mounting unit and corrects the magnification of the transmission image of the object to be measured according to a deflection amount of the mounting unit caused by mounting the object to be measured upon the mounting unit.

2. An X-ray apparatus, comprising:
a mounting unit upon which an object to be measured is mounted;
an X-ray generator that irradiates X-rays, from above the mounting unit or from below the mounting unit, to the object to be measured that is mounted upon the mounting unit;
a mark for magnification measurement that is formed upon a mounting surface of a region or upon an underside surface of the region of the mounting unit, the object to be measured being mounted on the region of the mounting unit;
an X-ray detector that acquires a transmission image of the object to be measured and a transmission image of the mark for magnification measurement, which are being irradiated by the X-rays;
a first movement unit that moves at least one of the mounting unit, the X-ray generator, and the X-ray detector along a direction of irradiation of the X-rays; and
a calculator that calculates a magnification of a transmission image of the object to be measured based on a transmission image of the mark for magnification measurement, wherein the transmission image of the object to be measured and the transmission image of the mark for magnification measurement detected by the X-ray detector appear upon the same projection image.

3. The X-ray apparatus according to claim 2, wherein the mark for magnification measurement is formed upon the mounting surface of the mounting unit.

4. The X-ray apparatus according to claim 3, wherein:
a contact detector that detects contact of the mounting unit against the X-ray generator, while the first movement unit moves at least one of the mounting unit and the X-ray generator; and wherein
the X-ray generator irradiates the X-rays against the object to be measured from below the mounting unit.

5. The X-ray apparatus according to claim 4, wherein:
the contact detector comprises an electrically conductive member that is provided upon the underside surface of the mounting unit, and an electrically conductive member that is provided upon the X-ray generator; and
the contact detector detects contact between the electrically conductive member that is provided upon the underside surface of the mounting unit and the electrically conductive member that is provided upon the X-ray generator unit electrically.

6. The X-ray apparatus according to claim 4, wherein the mark for magnification measurement comprises an electrically conductive member that is formed upon the rear surface of the mounting unit.

7. The X-ray apparatus according to claim 2, further comprising
an extraction unit that extracts a transmission image of the mark for magnification measurement from a transmission image of the object to be measured and a transmission image of the mark for magnification measurement; and wherein
the calculator calculates the magnification of the transmission image of the object to be measured based on the transmission image of the mark for magnification measurement extracted by the extraction unit.

8. The X-ray apparatus according to claim 2, wherein
if distortion has been occurred in the mark for magnification measurement along with deflection of the mounting unit occurred by mounting the object to be measured on the mounting unit, the calculator corrects the magnification of the transmission image of the object to be measured based on the transmission image of the mark for magnification measurement in which the distortion has been occurred, and the state of distortion of the mark for magnification measurement.

9. An X-ray apparatus, comprising:
a mounting unit upon which an object to be measured is mounted;
an X-ray generator that irradiates X-rays, from above the mounting unit or from below the mounting unit, to the object to be measured that is mounted upon the mounting unit;
a mark for magnification measurement that is formed upon a mounting surface or upon an underside surface of the mounting unit;

an X-ray detector that acquires a transmission image of the object to be measured and a transmission image of the mark for magnification measurement, which are being irradiated by the X-rays;
a first movement unit that moves at least one of the mounting unit, the X-ray generator, and the X-ray detector along a direction of irradiation of the X-rays;
a position detector that detects a relative position of the mounting unit, the X-ray generator, and the X-ray detector;
a first calculator that calculates a magnification of a transmission image of the object to be measured based on the relative position detected by the position detector;
a second calculator that calculates the magnification of a transmission image of the object to be measured based on a transmission image of the mark for magnification measurement acquired by the X-ray detector; and
a control unit that selects either the first calculator or the second calculator to calculate the magnification of the object to be measured; and wherein
when the magnification corresponding to the relative position detected by the position detector is smaller than a predetermined value, the control unit causes the first calculator to calculate the magnification of the object to be measured, and when the magnification corresponding to the relative position detected by the position detector is greater than the predetermined value, the control unit causes the second calculator to calculate the magnification of the object to be measured.

10. The X-ray apparatus according to claim 9, further comprising
a contact detector that detects contact of the mounting unit against the X-ray generator, while the first movement unit moves at least one of the mounting unit and the X-ray generator; and wherein:
the X-ray generator irradiates the X-rays against the object to be measured from below the mounting unit;
the mark for magnification measurement is formed upon the underside surface of the mounting unit; and
the contact detector detects that the mark for magnification measurement has contacted to the X-ray generator.

11. The X-ray apparatus according to claim 10, wherein:
the mark for magnification measurement comprises an electrically conductive member;
the X-ray generator comprises an electrically conductive member; and
the contact detector detects contact between the mark for magnification measurement and the electrically conductive member comprised in the X-ray generator electrically.

12. The X-ray apparatus according to claim 1, further comprising
a reconstruction unit that creates internal structural information about the object to be measured based on a plurality of transmission images detected by the X-ray detector, in a state in which the positions of the X-ray generator and the X-ray detector with respect to the object to be measured are different.

13. A structure production method, comprising:
creating design information related to a shape of a structure;
forming the structure based on the design information;
acquiring shape information by measuring the shape of the structure, which has been formed, by using the X-ray apparatus according to claim 1; and
comparing the shape information that has been acquired and the design information.

14. The structure production method according to claim 13, further comprising
performing re-processing of the structure based on a result of comparison of the shape information and the design information.

15. The structure production method according to claim 14, wherein
the re-processing of the structure comprises again performing formation of the structure based on the design information.

16. The X-ray apparatus according to claim 1, further comprising
a proximity detector that detects contact between or proximity of a deflected region occurred on the mounting unit and the X-ray generator; and wherein
the calculator calculates the corrected magnification when the contact or the proximity is detected by the proximity detector.

17. The X-ray apparatus according to claim 16, wherein
the proximity detector comprises a first electrically conductive member that is provided upon a surface of the mounting unit that opposes the X-ray generator and a second electrically conductive member that is provided upon the X-ray generator, and detects contact between the first and second conductive members electrically.

18. The X-ray apparatus according to claim 16, further comprising
a position detector that detects a relative position of the mounting unit relative to the X-ray generator or the X-ray detector; and wherein
the calculator calculates the magnification of the transmission image of the object to be measured based upon the relative position, the transmission image to be acquired by the X-ray detector.

19. The X-ray apparatus according to claim 18, wherein:
based upon the relative position detected by the position detector when the contact or the proximity is detected by the proximity detector, the calculator performs a correction process in which the corrected magnification is calculated by correcting the magnification of the transmission image of the object to be measured.

20. The X-ray apparatus according to claim 1, further comprising
a deflection detection unit that detects the deflection amount of the mounting unit while the object to be measured is mounted upon the mounting unit; and wherein
the calculator calculates the magnification of the transmission image of the object to be measured based on the position detected by the position detector and the deflection amount detected by the deflection detection unit.

21. The X-ray apparatus according to claim 20, further comprising
a first movement unit that moves at least one of the mounting unit, the X-ray generator, and the X-ray detector along a direction of irradiation of the X-ray.

22. The X-ray apparatus according to claim 21, wherein
the magnification is set by the first movement unit moving at least one of the mounting unit, the X-ray generator, and the X-ray detector to a predetermined position.

23. The X-ray apparatus according to claim 21, wherein a second movement unit that moves at least one of the mounting unit and the X-ray generator in a plane that intersects a direction of movement by the first movement unit.

24. The X-ray apparatus according to claim 1, wherein the deflection of the mounting unit is occurred by mounting the object to be measured upon the mounting unit.

* * * * *